United States Patent
Yamanaka et al.

(10) Patent No.: US 10,240,126 B2
(45) Date of Patent: Mar. 26, 2019

(54) INDUCED PLURIPOTENT STEM CELL SELECTION METHOD AND METHOD FOR INDUCING DIFFERENTIATION TO BLOOD CELLS

(71) Applicant: KYOTO UNIVERSITY, Kyoto-shi, Kyoto (JP)

(72) Inventors: Shinya Yamanaka, Kyoto (JP); Yoshinori Yoshida, Kyoto (JP); Masatoshi Nishizawa, Kyoto (JP)

(73) Assignee: KYOTO UNIVERSITY, Kyoto-Shi, Kyoto (JP)

( * ) Notice: Subject to any disclaimer, the term of this patent is extended or adjusted under 35 U.S.C. 154(b) by 0 days.

(21) Appl. No.: 14/897,599

(22) PCT Filed: Jun. 11, 2014

(86) PCT No.: PCT/JP2014/065497
§ 371 (c)(1),
(2) Date: Dec. 10, 2015

(87) PCT Pub. No.: WO2014/200030
PCT Pub. Date: Dec. 18, 2014

(65) Prior Publication Data
US 2016/0137981 A1    May 19, 2016

(30) Foreign Application Priority Data
Jun. 12, 2013 (JP) ................................ 2013-123485

(51) Int. Cl.
*C12N 5/00* (2006.01)
*C12N 5/02* (2006.01)
*C12N 5/074* (2010.01)
*C12N 15/86* (2006.01)
*C12N 5/0789* (2010.01)
*G01N 33/569* (2006.01)
*C12Q 1/6881* (2018.01)
*C07K 14/65* (2006.01)

(52) U.S. Cl.
CPC ............ *C12N 5/0647* (2013.01); *C07K 14/65* (2013.01); *C12N 5/0696* (2013.01); *C12Q 1/6881* (2013.01); *G01N 33/56966* (2013.01); *C12N 2501/105* (2013.01); *C12N 2501/115* (2013.01); *C12N 2501/125* (2013.01); *C12N 2501/14* (2013.01); *C12N 2501/145* (2013.01); *C12N 2501/155* (2013.01); *C12N 2501/165* (2013.01); *C12N 2501/2303* (2013.01); *C12N 2501/2306* (2013.01); *C12N 2501/2311* (2013.01); *C12N 2501/26* (2013.01); *C12N 2506/45* (2013.01); *C12N 2510/00* (2013.01); *C12Q 2600/158* (2013.01)

(58) Field of Classification Search
CPC .............. C07K 14/65; C12N 2501/105; C12N 2501/115; C12N 2501/125; C12N 2501/14; C12N 2501/145; C12N 2501/155; C12N 2501/165; C12N 2501/2303; C12N 2501/2306; C12N 2501/2311; C12N 2501/26
USPC ........ 435/377, 325, 375, 287.1, 287.2, 288.7, 435/289.1, 366, 455, 456, 7.21
See application file for complete search history.

(56) References Cited

U.S. PATENT DOCUMENTS

| | | | |
|---|---|---|---|
| 5,843,780 A | 12/1998 | Thomson | |
| 2009/0068742 A1 | 3/2009 | Yamanaka | |
| 2013/0011924 A1 | 1/2013 | Niwa et al. | |
| 2015/0118230 A1* | 4/2015 | Seong | C07K 14/4701 424/135.1 |
| 2015/0329821 A1* | 11/2015 | Ang | C12N 5/0606 435/366 |
| 2016/0146788 A1* | 5/2016 | Yamanaka | G01N 33/5011 424/93.7 |

FOREIGN PATENT DOCUMENTS

| | | |
|---|---|---|
| WO | WO 2007/069666 A1 | 6/2007 |
| WO | WO 2008/151390 A1 | 12/2008 |
| WO | WO 2011/115308 A1 | 9/2011 |
| WO | WO 2012/037456 A1 | 3/2012 |
| WO | WO 2013122408 A1 * | 8/2013 ......... C07K 14/4701 |

OTHER PUBLICATIONS

International Search Report for International Application No. PCT/JP2014/065497, dated Jul. 22, 2014.
Bock et al., "Reference Maps of Human ES and iPS Cell Variation Enable High-Throughput Characterization of Pluripotent Cell Lines," *Cell*, vol. 144(3), pp. 439-452 (Feb. 4, 2011).
Chadwick et al., "Cytokines and BMP-4 promote hematopoietic differentiation of human embryonic stem cells," *Blood*, vol. 102(3), pp. 906-915 (Aug. 1, 2003).
Hiroyama et al., "Long-lasting in vitro hematopoiesis derived from primate embryonic stem cells," *Experimental Hematology*, vol. 34(6), pp. 760-769 (2006).
Kennedy et al., "Development of the hemangioblast defines the onset of hematopoiesis in human ES cell differentiation cultures," *Blood*, vol. 109(7), pp. 2679-2687 (Apr. 1, 2007).

(Continued)

*Primary Examiner* — Janet L Epps-Smith
(74) *Attorney, Agent, or Firm* — Knobbe, Martens, Olson & Bear, LLP

(57) ABSTRACT

A method for producing hematopoietic stem cells and/or hematopoietic progenitor cells from pluripotent stem cells is described. The method includes a step of culturing pluripotent stem cells in the presence of IGF2. A method is described for selecting an induced pluripotent stem cell(s) having high capacity to differentiate into hematopoietic stem cells and/or hematopoietic progenitor cells, or into blood cells, based on the expression level(s) of one or more genes such as TRIM58, CTSF, FAM19A5, and TCERG1L genes, or on the DNA methylation state(s) of the TRIM58, CSMD1, and/or FAM19A5 gene(s).

17 Claims, 2 Drawing Sheets
Specification includes a Sequence Listing.

(56) References Cited

OTHER PUBLICATIONS

Kim et al., "Epigenetic memory in induced pluripotent stem cells," *Nature*, vol. 467(7313), pp. 285-290 (2010).

Niwa et al., "Orderly Hematopoietic Development of Induced Pluripotent Stem Cells via Flk-1+Hemoangiogenic Progenitors," *Journal of Cellular Physiology*, vol. 221, pp. 367-377 (2009).

Ramos-Mejia et al., "Nodal/Activin Signaling Predicts Human Pluripotent Stem Cell Lines Prone to Differentiate Toward the Hematopoietic Lineage," *Molecular Therapy*, vol. 18(12), pp. 2173-2181 (Dec. 2010).

Takayama et al., "Generation of functional platelets from human embryonic stem cells in vitro via ES-sacs, VEGF-promoted structures that concentrate hematopoietic progenitors," *Blood*, vol. 111(11), pp. 5298-5306 (Jun. 1, 2008).

The Office Action dated Jun. 12, 2018 of the corresponding Japanese Patent Application No. 2015-522837 with its machine translation.

The Most Trusted Cytogenetics Research Solutions, Cytogenetics Catalog, Agilent Technologies, Jun. 1, 2012, pp. 1-17.

* cited by examiner

[Fig. 1]
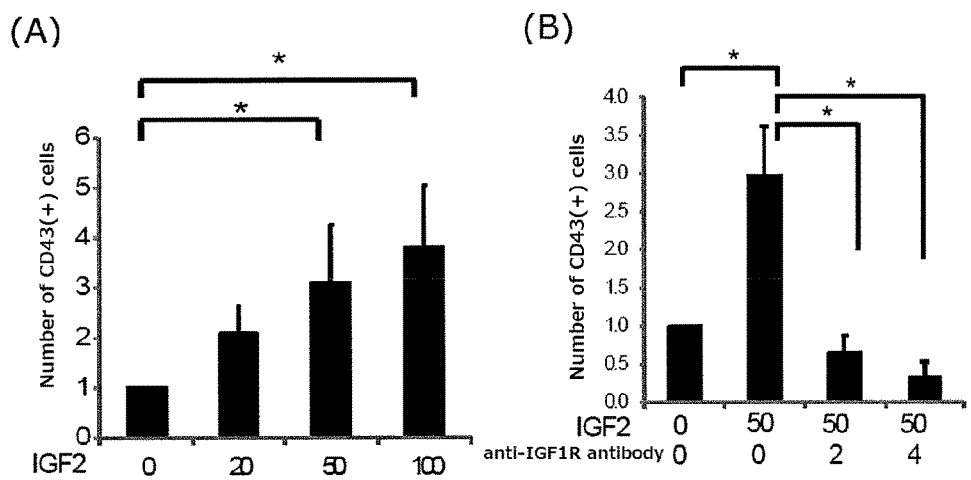
[Fig. 2]
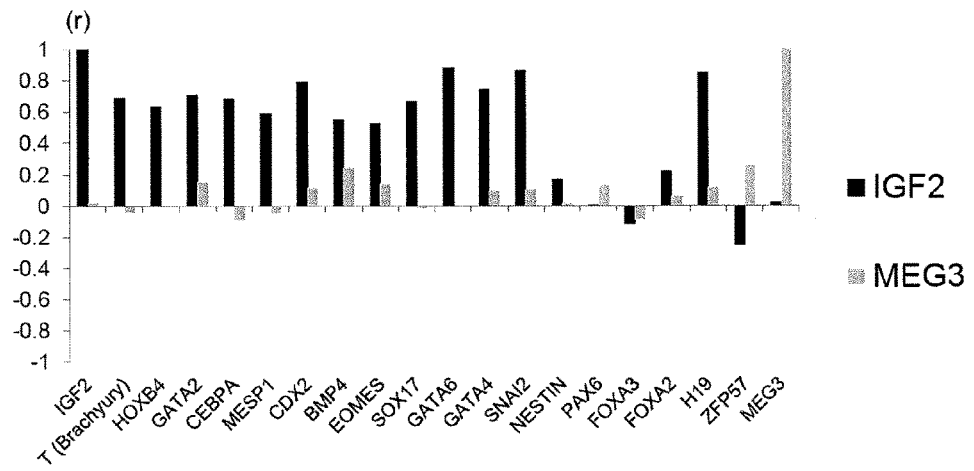

[Fig. 3]
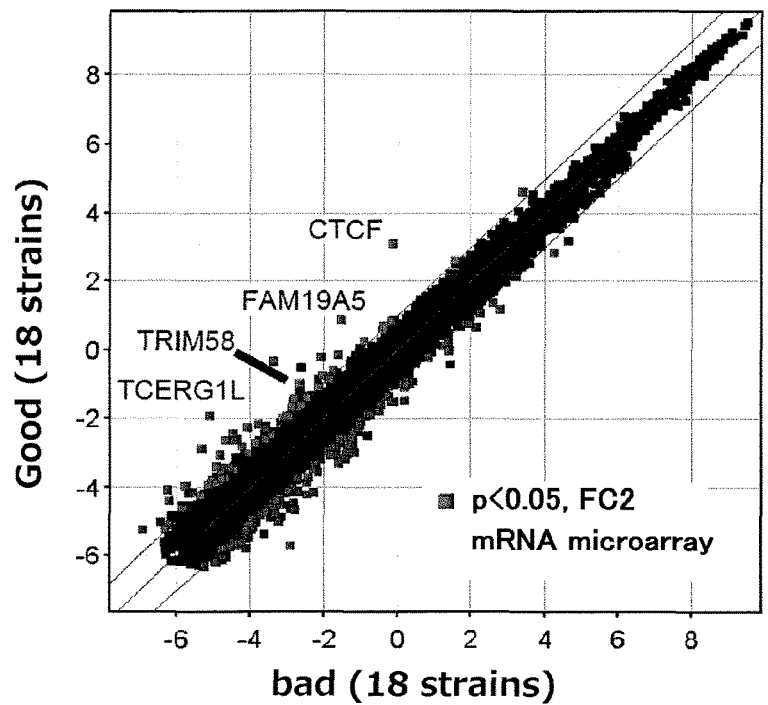
[Fig. 4]
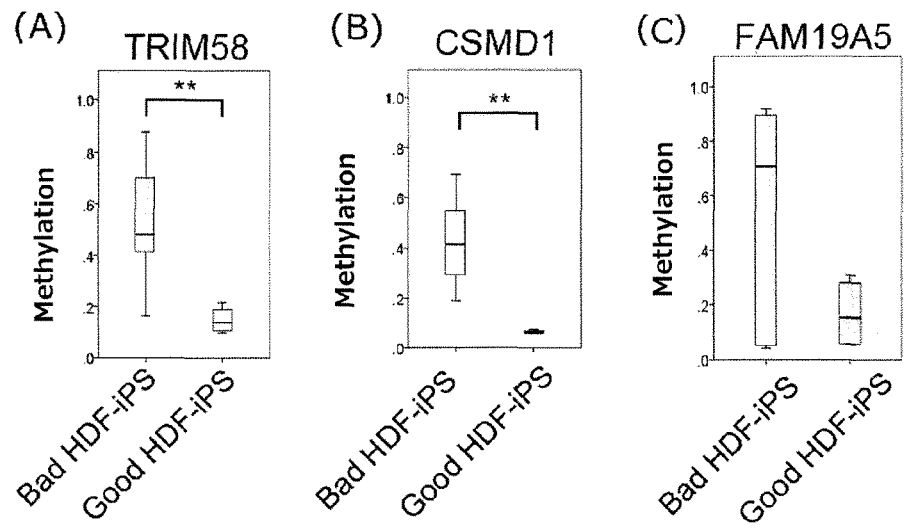

INDUCED PLURIPOTENT STEM CELL SELECTION METHOD AND METHOD FOR INDUCING DIFFERENTIATION TO BLOOD CELLS

CROSS-REFERENCE TO RELATED APPLICATIONS

This application is the U.S. National Phase under 35 U.S.C. § 371 of International Application PCT/JP2014/065497, filed Jun. 11, 2014, which claims priority to JP 2013-123485, filed Jun. 12, 2013.

REFERENCE TO SEQUENCE LISTING

This application incorporates by reference the sequence listing submitted as ASCII text filed via EFS-Web on Dec. 10, 2015. The Sequence Listing is provided as a file entitled "sequence_listing_toya166018apc.txt," created on Dec. 10, 2015, and which is approximately 33 kilobytes in size.

TECHNICAL FIELD

The present invention relates to a novel method for producing hematopoietic stem cells and/or hematopoietic progenitor cells; and a method for promoting induction of differentiation into, and a promoter for induction of differentiation into, hematopoietic stem cells and/or hematopoietic progenitor cells. The present invention also relates to a method for selecting an induced pluripotent stem cell(s) showing high efficiency of differentiation into hematopoietic stem cells and/or hematopoietic progenitor cells, and a reagent, microarray, and kit therefor. The present invention also relates to a method for selecting an induced pluripotent stem cell(s) having high capacity to differentiate into blood cells, and a reagent, microarray, and kit therefor

BACKGROUND ART

In treatment of blood-related diseases such as leukemia, and in surgical treatment, it is very important to stably amplify and supply blood cells in an amount necessary for the treatment. For this purpose, a number of medical workers have devised various means for securing the blood cells. For example, collection of blood from donors and induction of differentiation from cord blood or bone marrow cells have been conventionally carried out.

In recent years, attempts are being made to efficiently amplify hematopoietic stem cells or hematopoietic progenitor cells, which can be used as a source for production of blood cells, using cells having pluripotency such as embryonic stem cells (ES cells) or induced pluripotent stem (iPS) cells obtained by introduction of undifferentiated-cell-specific genes into somatic cells (e.g., Patent Documents 1 and 2).

Examples of methods for inducing differentiation of ES cells or iPS cells into hematopoietic stem cells and/or hematopoietic progenitor cells that have been reported so far include a method by formation of embryoid bodies and addition of cytokine (Non-patent Document 1), a method by co-culture with stromal cells derived from a different species (Non-patent Document 2), and a method using a serum-free medium (Patent Document 3).

However, further improvement is necessary for enabling their application to medical treatment, and establishment of more efficient methods for differentiation induction, identification of novel differentiation-inducing factors, and methods for selecting productive cells in a stage before carrying out differentiation induction treatment, are demanded.

PRIOR ART DOCUMENTS

Patent Documents

[Patent Document 1] U.S. Pat. No. 5,843,780
[Patent Document 2] WO 2007/069666
[Patent Document 3] WO 2011/115308

Non-Patent Documents

[Non-patent Document 1] Chadwick et al. Blood 2003, 102: 906-15
[Non-patent Document 2] Niwa A et al. J Cell Physiol. 2009 November; 221(2): 367-77

SUMMARY OF THE INVENTION

An object of the present invention is to provide a novel method for producing hematopoietic stem cells and/or hematopoietic progenitor cells, and a novel factor to promote differentiation induction into hematopoietic stem cells and/or hematopoietic progenitor cells. Another object of the present invention is to provide a method for selecting an induced pluripotent stem cell(s) showing high efficiency of differentiation into hematopoietic stem cells and/or hematopoietic progenitor cells. Still another object of the present invention is to provide a method for selecting an induced pluripotent stem cell(s) having high capacity to differentiate into blood cells.

The present inventors intensively studied to solve the above-described problem, and, as a result, discovered that induction of differentiation of pluripotent stem cells into hematopoietic stem cells and/or hematopoietic progenitor cells is promoted by addition of IGF2 (insulin-like growth factor 2).

Further, by comparing RNAs collected from iPS/ES cell lines having high capacity to differentiate into blood cells (Good lines) and iPS/ES cell lines having low capacity to differentiate into blood cells (Bad lines), the present inventors discovered that genes such as CTSF, FAM19A5, TRIM58, and TCERG1L show positive correlations with the Good lines. Subsequently, by comparing the methylation state between the genomes of the Good lines and the Bad lines, the present inventors discovered that high numbers of mixed colonies (that is, high capacity of iPS/ES cells lines to differentiate into blood cells) show positive correlations with low methylation states of TRIM58, CSMD1, and FAM19A5.

The present invention was completed based on such discoveries.

That is, the present invention provides the followings.

[1] A method for selecting an iPS cell(s) having high capacity to differentiate into blood cells, the method comprising the steps of:

(i) measuring the expression level(s) of one or more genes selected from the group consisting of TRIM58, CTSF, FAM19A5, and TCERG1L genes in sample induced pluripotent stem cells; and (ii) selecting an induced pluripotent stem cell(s) in which the expression level(s) of the gene(s) measured as described above is/are equivalent to or higher than the expression level(s) in iPS cells or ES cells which are known to have high capacity to differentiate into blood cells, and/or selecting an induced pluripotent stem cell(s) in which the expression level(s) of the gene(s) measured as described above is/are higher than the expression level(s) in iPS cells or ES cells which are known to have low capacity to differentiate into blood cells.

[2] A method for selecting an induced pluripotent stem cell(s) having high capacity to differentiate into blood cells, the method comprising the steps of:

(i) measuring the DNA methylation state(s) of TRIM58, CSMD1, and/or FAM19A5 gene(s) in sample induced pluripotent stem cells; and (ii) selecting an induced pluripotent stem cell(s) in which the DNA methylation level(s) measured as described above is/are equivalent to or lower than the DNA methylation level(s) in iPS cells or ES cells which are known to have high capacity to differentiate into blood cells, and/or selecting an induced pluripotent stem cell(s) in which the DNA methylation level(s) measured as described above is/are lower than the DNA methylation level(s) in iPS cells or ES cells which are known to have low capacity to differentiate into blood cells.

[3] The method according to [1] or [2], wherein the blood cells are one or more kinds of cells selected from the group consisting of erythrocytes, platelets, monocytes, T cells, B cells, NK cells, neutrophils, eosinophils, basophils, granulocytes, and macrophages.

[4] The method according to any of [1] to [3], wherein the sample induced pluripotent stem cells are human iPS cells.

[5] The method according to any of [1] to [4], wherein the iPS cells or ES cells which are known to have high capacity to differentiate into blood cells are one or more types of cells selected from the group consisting of 751A3, 783F1, 751B4, 692D2, 783A2, 744A2, 744B9, 609A2, 585B1, 784D1, 609A1, 648B1, 665A7, 451F3, 610B1, 606A1, 648A1, and khES3.

[6] The method according to any of [1] to [5], wherein the iPS cells or ES cells which are known to have low capacity to differentiate into blood cells are one or more kinds of cells selected from the group consisting of 427F1, khES1, TIG1204F1, H9, Kep1, 454E2, 253G1, KRV-1, 457C1, 7-KE2, 201B7, TIG1074F1, 246G1, 409B2, 201B6, 253G4, 404C2, and 588A4.

[7] A kit for selecting an induced pluripotent stem cell(s) having high capacity to differentiate into blood cells, the kit comprising a nucleic acid(s) and/or artificial nucleic acid(s) complementary to a sequence(s) of TRIM58, CTSF, FAM19A5, and/or TCERG1L gene(s).

[8] The kit according to [7], wherein the complementary nucleic acid(s) is/are provided as a microarray(s).

[9] A method for producing hematopoietic stem cells and/or hematopoietic progenitor cells from pluripotent stem cells, the method comprising a step of culturing the pluripotent stem cells in the presence of insulin-like growth factor 2 (IGF2).

[10] The method according to [9], wherein the step of culturing pluripotent stem cells in the presence of IGF2 comprises the steps of:

(i) culturing pluripotent stem cells in a medium supplemented with BMP4 and IGF2;

(ii) culturing cells obtained in Step (i) in a medium supplemented with BMP4, bFGF, and IGF2;

(iii) culturing cells obtained in Step (ii) in a medium supplemented with VEGF, bFGF, IL-6, IL-3, IL-11, SCF, Flt3L, and IGF2; and (iv) culturing cells obtained in Step (iii) in a medium supplemented with VEGF, IL-6, IL-3, IL-11, SCF, Flt3L, EPO, TPO, and IGF2.

[11] The method according to [9] or [10], wherein, in the step of culturing pluripotent stem cells, the pluripotent stem cells are cultured in a form of embryoid bodies.

[12] The method according to any of [9] to [11], wherein the pluripotent stem cells are iPS cells.

[13] The method according to [12], wherein the iPS cells are human iPS cells.

[14] The method according to [12] or [13], wherein the iPS cells are iPS cells selected by the steps of:

(1) measuring the expression level(s) of one or more genes selected from the group consisting of TRIM58, CTSF, FAM19A5, and TCERG1L genes in candidate iPS cells; and (2) selecting an iPS cell(s) based on the expression level(s) measured in Step (1).

[15] The method according to [12] or [13], wherein the iPS cells are iPS cells selected by the steps of:

(1) measuring the DNA methylation state(s) of TRIM58, CSMD1, and/or FAM19A5 gene(s) in candidate iPS cells; and (2) selecting an iPS cell(s) based on the DNA methylation state(s) measured in Step (1).

[16] A promoter for induction of differentiation of pluripotent stem cells into hematopoietic stem cells and/or hematopoietic progenitor cells, the promoter comprising IGF2 as an effective component.

Effect of the Invention

By the present invention, differentiation of pluripotent stem cells into hematopoietic stem cells and/or hematopoietic progenitor cells can be more efficiently induced. In addition, undifferentiated iPS cells in a stage before differentiation induction can be evaluated for their capacity to differentiate into blood (their efficiency of differentiation into hematopoietic stem cells and/or hematopoietic progenitor cells, and their capacity to differentiate into blood cells). Thus, the present invention can provide efficient supply of a large amount of blood-related cells, and is therefore extremely useful from the viewpoint of industrial application.

BRIEF DESCRIPTION OF THE DRAWINGS

FIG. 1 shows the effect of IGF2 on induction of differentiation of human iPS cells into hematopoietic progenitor cells. (A) Comparison was made among four groups in which the concentration of IGF2 was 0 ng/ml (no addition), 20 ng/ml, 50 ng/ml, or 100 ng/ml. (B) IGF2 (50 ng/ml) was added together with an anti-IGF1R antibody to confirm that the induction of differentiation into hematopoietic progenitor cells was due to the effect of IGF2.

FIG. 2 shows results of search for genes whose expression changes in correlation with IGF2. The analysis was carried out by SPSS statistics (IBM), wherein significance for each gene was assumed at $P<0.05$ (unpaired t-test). Correlation of expression among the genes was analyzed using the Pearson correlation coefficient (wherein the correlation coefficient is represented as r).

FIG. 3 shows results of microarray-based comparison of expression of genes in relation to differences in the capacity to differentiate into blood cells. Human iPS cell lines and human ES cell lines were divided into a group of cells showing high capacity to differentiate into blood cells and a group of cells showing low capacity to differentiate into blood cells. A scatter plot for comparison of the pattern of gene expression between these groups is shown. The straight line indicates a 5-fold or more increase in the gene expression level. In the diagram, Good represents cells having high capacity to differentiate into blood cells, and Bad represents cells having low capacity to differentiate into blood cells.

FIG. 4 shows results of analysis comparing the methylation state of the genome in relation to differences in the capacity to differentiate into blood cells. The low methylation states of TRIM58, CSMD1, and FAM19A5 were found to be positively correlated with the large numbers of mixed colonies.

EMBODIMENTS FOR CARRYING OUT THE INVENTION

The present invention is described below in detail.

The present invention provides a method for producing hematopoietic stem cells and/or hematopoietic progenitor cells from pluripotent stem cells, which method comprises a step of culturing the pluripotent stem cells in the presence of IGF2.

In the present invention, the IGF2 is preferably human IGF2, and examples of the human IGF2 include the basic peptide of 67 amino acids produced by processing from the protein having the sequence shown as NCBI Accession No. NP_000603. IGF2 is available from Sigma-Aldrich or PeproTech.

<Pluripotent Stem Cells>

The pluripotent stem cells which may be used in the present invention are stem cells having pluripotency which enables the cells to differentiate into any cells existing in the living body, which pluripotent stem cells also have growth ability. Examples of the pluripotent stem cells include, but are not limited to, embryonic stem (ES) cells, embryonic stem cells derived from a cloned embryo obtained by nuclear transfer ("ntES cells"), germline stem cells ("GS cells"), embryonic germ cells ("EG cells"), and induced pluripotent stem (iPS) cells. Preferred examples of the pluripotent stem cells include ES cells, ntES cells and iPS cells.

(A) Embryonic Stem Cells

ES cells are stem cells established from the inner cell mass of an early embryo (for example, blastocyst) of a mammal such as human or mouse, which cells have pluripotency and growth ability by self-renewal.

ES cells are embryo-derived stem cells originated from the inner cell mass of a blastocyst which is an embryo formed following the 8-cell stage and the formula stage of a fertilized egg, and have ability to differentiate into any cells constituting an adult, that is, the so called pluripotency of differentiation, and growth ability by self-renewal. ES cells were discovered in mouse in 1981 (M. J. Evans and M. H. Kaufman (1981), Nature 292: 154-156), and this was followed by establishment of ES cell lines of primates such as human and monkey (J. A. Thomson et al. (1998), Science 282: 1145-1147; J. A. Thomson et al. (1995), Proc. Natl. Acad. Sci. USA, 92: 7844-7848; J. A. Thomson et al. (1996), Biol. Reprod., 55: 254-259; and J. A. Thomson and V. S. Marshall (1998), Curr. Top. Dev. Biol., 38: 133-165).

ES cells can be established by removing the inner cell mass from the blastocyst of a fertilized egg of a subject animal, followed by culturing the inner cell mass on fibroblasts as feeders. The cells can be maintained by subculturing using a culture medium supplemented with substances such as leukemia inhibitory factor (LIF) and basic fibroblast growth factor (bFGF). Methods of establishment and maintenance of human and monkey ES cells are described in, for example, H. Suemori et al. (2006), Biochem. Biophys. Res. Commun., 345: 926-932; M. Ueno et al. (2006), Proc. Natl. Acad. Sci. USA, 103: 9554-9559; H. Suemori et al. (2001), Dev. Dyn., 222: 273-279; and H. Kawasaki et al. (2002), Proc. Natl. Acad. Sci. USA, 99: 1580-1585.

In terms of the culture medium for preparation of ES cells, human ES cells can be maintained, for example, using DMEM/F-12 medium supplemented with 0.1 mM 2-mercaptoethanol, 0.1 mM non-essential amino acids, 2 mM L-glutamic acid, 20% KSR and 4 ng/ml bFGF, at 37° C. under a moist atmosphere with 5% $CO_2$. Further, ES cells need to be subcultured every 3 to 4 days, and the subculture can be carried out using, for example, 0.25% trypsin and 0.1 mg/ml collagenase IV in PBS supplemented with 1 mM $CaCl_2$ and 20% KSR.

Selection of ES cells can be generally carried out using expression of a gene marker(s) such as alkaline phosphatase, Oct-3/4, and/or Nanog as an index/indices. In particular, selection of human ES cells can be carried out by detecting expression of a gene marker(s) such as OCT-3/4 and/or NANOG by Real-Time PCR, or by detecting a cell surface antigen(s) SSEA-3, SSEA-4, TRA-1-60, and/or TRA-1-81 by immunostaining (Klimanskaya I, et al. (2006), Nature. 444: 481-485).

Human ES cell lines such as KhES-1, KhES-2, and KhES-3 can be obtained from Institute for Frontier Medical Sciences, Kyoto University (Kyoto, Japan).

(B) Germline Stem Cells

Germline stem cells are pluripotent stem cells derived from testis, and play a role as the origin for spermatogenesis. Similarly to ES cells, these cells can be induced to differentiate into various series of cells, and, for example, have a property to enable preparation of a chimeric mouse by transplanting the cells to a mouse blastocyst (M. Kanatsu-Shinohara et al. (2003) Biol. Reprod., 69: 612-616; K. Shinohara et al. (2004), Cell, 119: 1001-1012). Germline stem cells are capable of self-renewal in a culture medium containing glial cell line-derived neurotrophic factor (GDNF), and, by repeating subculture under the same culture conditions as those for ES cells, germline stem cells can be obtained (Masanori Takehashi et al. (2008), Experimental Medicine, 26(5) (extra edition), 41-46, Yodosha (Tokyo, Japan)).

(C) Embryonic Germ Cells

Embryonic germ cells are established from fetal primordial germ cells and have pluripotency similarly to ES cells. They can be established by culturing primordial germ cells in the presence of substances such as LIF, bFGF and stem cell factor (Y. Matsui et al. (1992), Cell, 70: 841-847; J. L. Resnick et al. (1992), Nature, 359: 550-551).

(D) Induced Pluripotent Stem Cells

Induced pluripotent stem (iPS) cells can be prepared by introducing certain specific nuclear reprogramming substances in the forms of DNAs or proteins to somatic cells, or by increasing expression of the endogenous mRNAs and proteins of the nuclear reprogramming substances by using an agent(s). iPS cells are somatic cell-derived artificial stem cells having properties almost equivalent to those of ES cells, such as pluripotency of differentiation and growth ability by self-renewal (K. Takahashi and S. Yamanaka (2006) Cell, 126: 663-676; K. Takahashi et al. (2007) Cell, 131: 861-872; J. Yu et al. (2007) Science, 318: 1917-1920; M. Nakagawa et al. (2008) Nat. Biotechnol., 26: 101-106; WO 2007/069666; and WO 2010/068955). The nuclear reprogramming substances are not restricted as long as these are genes specifically expressed in ES cells, or genes playing important roles in maintenance of the undifferentiated state of ES cells, or gene products thereof, and examples thereof include Oct3/4, Klf4, Klf1, Klf2, Klf5, Sox2, Sox1, Sox3, Sox15, Sox17, Sox18, c-Myc, L-Myc, N-Myc, TERT, SV40 Large T antigen, HPV16 E6, HPV16 E7, Bmil, Lin28, Lin28b, Nanog, Esrrb, and Esrrg. These reprogramming substances may be used in combination when iPS cells are to be established. For example, the combination may contain at least one, two or three of the above reprogramming substances, and the combination preferably contains four of the above reprogramming substances.

The information on the nucleotide sequences of mouse and human cDNAs of the above-described respective nuclear reprogramming substances, and the amino acid sequences of the proteins encoded by the cDNAs can be obtained by referring to the NCBI accession numbers described in WO 2007/069666. Further, the information on the mouse and human cDNA sequences and amino acid sequences of each of L-Myc, Lin28, Lin28b, Esrrb, Esrrg, and Glis1 can be obtained by referring to the NCBI accession numbers described below. Those skilled in the art can prepare desired nuclear reprogramming substances by a conventional method based on the information on the cDNA sequences or amino acid sequences.

| Gene name | Mouse | Human |
| --- | --- | --- |
| L-Myc | NM_008506 | NM_001033081 |
| Lin28 | NM_145833 | NM_024674 |
| Lin28b | NM_001031772 | NM_001004317 |
| Esrrb | NM_011934 | NM_004452 |
| Esrrg | NM_011935 | NM_001438 |
| Glis1 | NM_147221 | NM_147193 |

These nuclear reprogramming substances may be introduced into somatic cells in the form of protein by a method such as lipofection, binding to a cell membrane-permeable peptide, or microinjection, or in the form of DNA by a method such as use of a vector including a virus, plasmid, and artificial chromosome; lipofection; use of liposomes; or microinjection. Examples of the virus vector include retrovirus vectors, lentivirus vectors (these are described in Cell, 126, pp. 663-676, 2006; Cell, 131, pp. 861-872, 2007; and Science, 318, pp. 1917-1920, 2007), adenovirus vectors (Science, 322, 945-949, 2008), adeno-associated virus vectors, and Sendai virus vectors (Proc Jpn Acad Ser B Phys Biol Sci. 85, 348-62, 2009). Examples of the artificial chromosome vector include human artificial chromosomes (HACs), yeast artificial chromosomes (YACs), and bacterial artificial chromosomes (BACs, PACs). Examples of the plasmid which may be used include plasmids for mammalian cells (Science, 322: 949-953, 2008). The vectors may contain a regulatory sequence(s) such as a promoter, enhancer, ribosome binding sequence, terminator, and/or polyadenylation site. Examples of the promoter to be used include the EF1α promoter, CAG promoter, SRα promoter, SV40 promoter, LTR promoter, CMV (cytomegalovirus) promoter, RSV (Rous sarcoma virus) promoter, MoMuLV (Moloney murine leukemia virus) LTR, and HSV-TK (herpes simplex virus thymidine kinase) promoter. Among these, the EF1α promoter, CAG promoter, MoMuLV LTR, CMV promoter, SRα promoter, and the like are preferred. The vectors may further contain, as required, a sequence of a selection marker such as a drug resistance gene (e.g., kanamycin-resistant gene, ampicillin-resistant gene, or puromycin-resistant gene), thymidine kinase gene, or diphtheria toxin gene; a gene sequence of a reporter such as the green-fluorescent protein (GFP), β-glucuronidase (GUS), or FLAG; or the like. Further, in order to remove, after introduction of the above vector into somatic cells, the genes encoding the nuclear reprogramming substances, or both the promoters and the genes encoding the reprogramming substances linked thereto, the vector may have loxP sequences in the upstream and the downstream of these sequences. In another preferred mode, a method may be employed wherein, after incorporation of the transgene(s) into a chromosome(s) using a transposon, transposase is allowed to act on the cells using a plasmid vector or an adenovirus vector, thereby completely removing the transgene(s) from the chromosome(s). Preferred examples of the transposon include piggyBac, which is a transposon derived from a lepidopteran insect (Kaji, K. et al., (2009), Nature, 458: 771-775; Woltjen et al., (2009), Nature, 458: 766-770; and WO 2010/012077). Further, the vector may contain the origin of lymphotrophic herpes virus, BK virus, or Bovine papillomavirus and sequences involved in their replication, such that the vector can replicate without incorporation into the chromosome and exist episomally. Examples of such a vector include vectors containing EBNA-1 and oriP sequences and vectors containing Large T and SV40ori sequences (WO 2009/115295; WO 2009/157201; WO 2009/149233). Further, in order to introduce plural nuclear reprogramming substances at the same time, an expression vector which allows polycistronic expression may be used. In order to allow polycistronic expression, the sequences encoding the genes may be linked to each other via IRES or the foot-and-mouth disease virus (FMDV) 2A coding region (Science, 322: 949-953, 2008; WO 2009/092042; and WO 2009/152529).

For enhancing the induction efficiency of iPS cells upon the nuclear reprogramming, histone deacetylase (HDAC) inhibitors [for example, low molecular inhibitors such as valproic acid (VPA) (Nat. Biotechnol., 26(7): 795-797 (2008)), trichostatin A, sodium butyrate, MC 1293, and M344; and nucleic acid-type expression inhibitors such as siRNAs and shRNAs against HDAC (e.g., HDAC1 siRNA Smartpool (registered trademark) (Millipore) and HuSH 29mer shRNA Constructs against HDAC1 (OriGene))], DNA methyltransferase inhibitors (e.g., 5'-azacytidine) (Nat. Biotechnol., 26(7): 795-797 (2008)), G9a histone methyltransferase inhibitors [for example, low molecular inhibitors such as BIX-01294 (Cell Stem Cell, 2: 525-528 (2008)); and nucleic acid-type expression inhibitors such as siRNAs and shRNAs against G9a (e.g., G9a siRNA (human) (Santa Cruz Biotechnology))], L-channel calcium agonists (e.g., Bayk8644) (Cell Stem Cell, 3, 568-574 (2008)), p53 inhibitors [e.g., siRNAs and shRNAs against p53 (Cell Stem Cell, 3, 475-479 (2008))], Wnt Signaling activators (e.g., soluble Wnt3a) (Cell Stem Cell, 3, 132-135 (2008)), growth factors such as LIF and bFGF, ALK5 inhibitors (e.g., SB431542) (Nat. Methods, 6: 805-8 (2009)), mitogen-activated protein kinase signaling inhibitors, glycogen synthase kinase-3 inhibitors (PLoS Biology, 6(10), 2237-2247 (2008)), miR-NAs such as miR-291-3p, miR-294, and miR-295 (R. L. Judson et al., Nat. Biotech., 27: 459-461 (2009)), and the like may be used in addition to the above-described factors.

Examples of the agent used in the method for increasing expression of the endogenous proteins of nuclear reprogramming substances using an agent include 6-bromoindirubin-3'-oxime, indirubin-5-nitro-3'-oxime, valproic acid, 2-(3-(6-methylpyridin-2-yl)-1H-pyrazol-4-yl)-1,5-naphthyridine, 1-(4-methylphenyl)-2-(4,5,6,7-tetrahydro-2-imino-3(2H)-benzothiazolyl)ethanone HBr (pifithrin-alpha), prostaglandin J2, and prostaglandin E2 (WO 2010/068955).

Examples of the culture medium for induction of the iPS cells include (1) DMEM, DMEM/F12, and DME supplemented with 10 to 15% FBS (these media may further contain LIF, penicillin/streptomycin, puromycin, L-glutamine, non-essential amino acids, β-mercaptoethanol, and/or the like, as appropriate); (2) culture media for ES cells containing bFGF or SCF, for example, culture media for mouse ES cells (e.g., TX-WES medium, Thromb-X), and culture media for primate ES cells (e.g., culture medium for primate (human and monkey) ES cells (ReproCELL Inc., Kyoto, Japan), mTeSR-1).

Examples of the culture method include a method wherein somatic cells and nuclear reprogramming substances (DNAs or proteins) are brought into contact with each other at 37° C. in the presence of 5% $CO_2$ in DMEM or DMEM/F12 medium supplemented with 10% FBS, and the cells are cultured for about 4 to 7 days, followed by replating the cells on feeder cells (e.g., mitomycin C-treated STO cells or SNL cells) and starting culture in a bFGF-containing culture medium for primate ES cells about 10 days after the contact between the somatic cells and the reprogramming substances, thereby allowing ES cell-like colonies to appear about 30 to about 45 days after the contact, or later. To enhance the induction efficiency of iPS cells, the culture may be carried out under conditions wherein the concentration of oxygen is as low as 5 to 10%.

As an alternative culture method, the somatic cells may be cultured on feeder cells (e.g., mitomycin C-treated STO cells or SNL cells) in DMEM medium supplemented with 10% FBS (which may further contain LIF, penicillin/streptomycin, puromycin, L-glutamine, non-essential amino acids, β-mercaptoethanol, and/or the like, as appropriate), thereby allowing ES-like colonies to appear after about 25 to about 30 days of the culture, or later.

During the above culture, the culture medium is replaced with a fresh culture medium once every day from Day 2 of the culture. The number of the somatic cells used for nuclear reprogramming is not restricted, and usually within the range of about $5 \times 10^3$ to about $5 \times 10^6$ cells per 100-$cm^2$ area on the culture dish.

In cases where a gene including a drug resistance gene is used as a marker gene, cells expressing the marker gene can be selected by culturing the cells in a culture medium (selection medium) containing the corresponding drug. Cells expressing a marker gene can be detected by observation under a fluorescence microscope in cases where the marker gene is the gene of a fluorescent protein; by adding a luminescent substrate in cases where the marker gene is the gene of luciferase; or by adding a coloring substrate in cases where the marker gene is the gene of a coloring enzyme.

The term "somatic cells" used in the present specification means any cells, excluding germ cells, derived from a mammal (e.g., human, mouse, monkey, pig, or rat). Examples of the somatic cells include epithelial cells which are keratinized (e.g., keratinized epidermal cells), mucosal epithelial cells (e.g., epithelial cells of the lingual surface), epithelial cells of exocrine glands (e.g., mammary cells), hormone-secreting cells (e.g., adrenomedullary cells), cells for metabolism and storage (e.g., hepatic cells), luminal epithelial cells constituting boundary surfaces (e.g., type I alveolar cells), luminal epithelial cells in the closed circulatory system (e.g., vascular endothelial cells), ciliated cells having a carrying capacity (e.g., tracheal epithelial cells), extracellular matrix-secreting cells (e.g., fibroblasts), contractile cells (e.g., smooth muscle cells), cells involved in the blood system and the immune system (e.g., T lymphocytes), sensory cells (e.g., rod cells), autonomic neurons (e.g., cholinergic neurons), supporting cells of sense organs and peripheral neurons (e.g., satellite cells), nerve cells and glial cells in the central nervous system (e.g., astroglial cells), and pigment cells (e.g., retinal pigment epithelial cells), and progenitor cells (tissue progenitor cells) thereof. The level of differentiation of the cells and the age of the animal from which the cells are collected are not restricted, and either undifferentiated progenitor cells (including somatic stem cells) or terminally-differentiated mature cells may be used as the source of the somatic cells in the present invention. Here, examples of the undifferentiated progenitor cells include tissue stem cells (somatic stem cells) such as neural stem cells, hematopoietic stem cells, mesenchymal stem cells, and dental pulp stem cells.

In the present invention, the mammalian individual from which somatic cells are derived is not restricted, and preferably human.

(E) ES Cells Derived from Cloned Embryo Obtained by Nuclear Transfer ntES cells are ES cells derived from a cloned embryo prepared by the nuclear transfer technique, and have almost the same properties as those in ES cells derived from fertilized eggs (T. Wakayama et al. (2001), Science, 292: 740-743; S. Wakayama et al. (2005), Biol. Reprod., 72: 932-936; J. Byrne et al. (2007), Nature, 450: 497-502). That is, an ntES (nuclear transfer ES) cell is an ES cell established from the inner cell mass of a blastocyst derived from a cloned embryo obtained by replacement of the nucleus of an unfertilized egg with the nucleus of a somatic cell. For preparation of an ntES cell, the combination of the nuclear transfer technique (J. B. Cibelli et al. (1998), Nature Biotechnol., 16: 642-646) and the ES cell preparation technique (described above) is employed (Sayaka Wakayama et al. (2008), Experimental Medicine 26(5) (extra edition), 47-52). In nuclear transfer, reprogramming can be achieved by injecting the nucleus of a somatic cell into a mammalian enucleated unfertilized egg and culturing the resultant for a several hours.

(F) Fused Stem Cells

These are stem cells prepared by fusing a somatic cell with an egg or an ES cell, and have the same pluripotency as that of the ES cell used for the fusion and also have genes specific to somatic cells (Tada M et al. Curr Biol. 11: 1553-8, 2001; Cowan C A et al. Science. 2005 Aug. 26; 309(5739): 1369-73).

Method for Inducing Differentiation into Hematopoietic Stem Cells and/or Hematopoietic Progenitor Cells Examples of the method for inducing differentiation of pluripotent stem cells into hematopoietic stem cells and/or hematopoietic progenitor cells include, but are not limited to, methods by formation of embryoid bodies and addition of cytokine (Chadwick et al. Blood 2003, 102: 906-15; Vijayaragavan et al. Cell Stem Cell 2009, 4: 248-62; and Saeki et al. Stem Cells 2009, 27: 59-67), a method by co-culture with stromal cells derived from a different species (Niwa A et al. J Cell Physiol. 2009 November; 221(2): 367-77), and a method using a serum-free medium (WO 2011/115308).

In the present invention, the terms "hematopoietic stem cell" and "hematopoietic progenitor cell" mean CD43-positive cells among cells committed to blood lineages.

In the present invention, the term "hematopoietic progenitor cell" means a cell whose differentiation has progressed compared to a "hematopoietic stem cell", and whose direction of differentiation has been determined. Hematopoietic progenitor cells can be detected based on expression of a marker(s) such as KDR, CD34, CD90, and/or CD117, although the markers are not limited to these. On the other hand, the term "hematopoietic stem cell" means a cell which is capable of producing a mature blood cell such as a T cell, B cell, erythrocyte, platelet, eosinophil, monocyte, neutrophil, or basophil, and has ability of self-renewal. In the present description, a "hematopoietic progenitor cell" is not distinguished from a "hematopoietic stem cell" unless otherwise specified.

In the present invention, the hematopoietic stem cells and/or hematopoietic progenitor cells obtained by differentiation induction may be provided as a cell population that also contains other cell species, or may be a purified population.

In the induction of hematopoietic progenitor cell in the present invention, pluripotent stem cells such as ES cells or iPS cells may be separated by an arbitrary method, and subjected to differentiation induction by suspension culture or by adherent culture using a coated culture dish. Examples of methods for separation of human pluripotent stem cells herein include a method by mechanical separation, and a separation method using a separation solution having protease activity and collagenase activity (e.g., Accutase™ or Accumax™) or a separation solution having only collagenase activity. The method is preferably a method comprising dissociating human pluripotent stem cells using a separation solution having protease activity and collagenase activity (especially preferably Accutase™), and then mechanically and finely dispersing the dissociated cells into single cells. The human pluripotent stem cells used in this method are preferably in the form of colonies cultured to 80% confluence with respect to the dish used. On the other hand, examples of methods for separation of mouse pluripotent stem cells include a separation method using 0.25% trypsin/EDTA.

The suspension culture herein means culturing of cells in a state where the cells are not adhering to the culture dish, to allow formation of embryoid bodies. The suspension culture is not limited, and may be carried out using a culture dish that is not artificially treated for the purpose of enhancing adhesiveness to cells (for example, by coating treatment with an extracellular matrix or the like), or using a culture dish that is treated such that adhesion is artificially suppressed (for example, by coating treatment with polyhydroxyethylmethacrylate (poly-HEMA)).

In cases where adherent culture is employed in the present invention, the cells may be cultured in an arbitrary medium on feeder cells or in a coated culture dish. The "feeder cells" herein means cells that play a supportive role to be used for adjusting culture conditions for the cells of interest. Examples of the feeder cells that may be used include cells obtained from the AGM region of a mammalian embryo (e.g., AGM-S3 cell line, JP 2001-37471 A), mouse mesenchymal cells (e.g., C3H10T1/2 cell line, available from Riken BioResource Center), and bone marrow-derived interstitial cells (stromal cells) (e.g., OP9 cell line). Examples of the coating agent include Matrigel (BD), collagen, gelatin, laminin, heparan sulfate proteoglycan, and entactin, and combinations thereof.

In the present invention, the medium for induction of hematopoietic progenitor cells may be prepared using, as a basal medium, a medium used for culturing animal cells. Examples of the basal medium include IMDM, Medium 199, Eagle's Minimum Essential Medium (EMEM), αMEM, Dulbecco's modified Eagle's Medium (DMEM), Ham's F12 medium, RPMI 1640 medium, Fischer's medium, StemPro34 (Invitrogen), and mixed media thereof. The medium may contain serum, or may be serum-free. The medium may contain, for example, if necessary, one or more of serum replacements such as albumin, transferrin, Knockout Serum Replacement (KSR) (serum replacement for FBS in ES cell culture), N2 supplement (Invitrogen), B27 supplement (Invitrogen), fatty acids, insulin, collagen precursor, trace elements, 2-mercaptoethanol (2ME), and thiolglycerol, and may also contain one or more of substances such as lipids, amino acids, L-glutamine, Glutamax (Invitrogen), non-essential amino acids, vitamins, growth factors, low-molecular-weight compounds, antibiotics, antioxidants, pyruvic acid, buffers, and inorganic salts.

In cases where adherent culture is employed in the present invention, the medium for differentiation into hematopoietic progenitor cells preferably contains vascular endothelial growth factor (VEGF). The concentration of VEGF in the medium is, for example, 1 ng/ml, 5 ng/ml, 10 ng/ml, 20 ng/ml, 30 ng/ml, 40 ng/ml, 50 ng/ml, 75 ng/ml, 100 ng/ml, 200 ng/ml, 300 ng/ml, 400 ng/ml, 500 ng/ml, or 1 µg/ml, but the concentration is not limited to these. The concentration of VEGF is preferably 20 ng/ml.

In cases where adherent culture is employed in the present invention, αMEM (also called HPC differentiation medium) supplemented with 10% FBS, VEGF, transferrin, L-glutamine, α-monothioglycerol (MTG), and ascorbic acid may be more preferred.

In cases where adherent culture is employed in the present invention, the number of days of culture is, for example, not more than 20 days, preferably 12 to 14 days, especially preferably 13 days.

In cases where adherent culture is employed in the present invention, a step of concentrating/purifying hematopoietic progenitor cells by removal of feeder cells may be included. This step can be achieved by peeling hematopoietic progenitor cells together with feeder cells from the culture dish, and then collecting and removing only feeder cells. Examples of the method of peeling from the culture dish include, but are not limited to, a method by mechanical separation, and a separation method using a separation solution having protease activity and collagenase activity or a separation solution having only collagenase activity. For example, a method using collagenase Type IV and/or Trypsin/EDTA is employed. In the method of separating hematopoietic progenitor cells, 0.05% trypsin/EDTA is preferably used.

In cases where suspension culture is employed in the present invention, the induction of differentiation into hematopoietic progenitor cells may be carried out by, for example, the steps of:
 (i) forming EBs;
 (ii) forming primitive streak/mesoderm;
 (iii) directing to hematopoietic progenitor cells; and
 (iv) growing and expanding the hematopoietic progenitor cells.

In each of the steps described above, a medium prepared by adding an arbitrary necessary substance(s) to a basic medium may be used for induction of cells of interest, or for achievement of the object of the step. For example, media supplemented with the following substances are used in each of the steps.
 (i) BMP-4;
 (ii) BMP4 and bFGF;
 (iii) VEGF, bFGF, IL-6, IL-3, IL-11, SCF, and Flt3L; and
 (iv) VEGF, IL-6, IL-3, IL-11, SCF, Flt3L, EPO, and TPO.

The basal medium to be used in the steps (i) to (iv) is preferably StemPro-34 supplemented with L-glutamic acid, thioglycerol, and ascorbic acid.

The concentration of BMP-4 in the medium for each of the steps (i) and (ii) is not limited as long as EBs can be formed. The concentration of BMP-4 is preferably 1 ng/ml to 100 ng/ml, for example, 1 ng/ml, 5 ng/ml, 10 ng/ml, 20 ng/ml, 30 ng/ml, 40 ng/ml, 50 ng/ml, 75 ng/ml, or 100 ng/ml, especially preferably 10 ng/ml.

The concentration of bFGF in the medium for each of the steps (ii) and (iii) is preferably 100 pg/ml to 20 ng/ml, for example, 100 pg/ml, 250 pg/ml, 500 pg/ml, 750 pg/ml, 1 ng/ml, 5 ng/ml, 10 ng/ml, or 20 ng/ml, but the concentration of bFGF is not limited to these. The concentration of bFGF in each step is especially preferably 1 ng/ml or 5 ng/ml.

The concentration of VEGF in the medium for each of the steps (iii) and (iv) is preferably 1 ng/ml to 100 ng/ml, for example, 1 ng/ml, 5 ng/ml, 10 ng/ml, 20 ng/ml, 30 ng/ml, 40 ng/ml, 50 ng/ml, 75 ng/ml, or 100 ng/ml, but the concentration of VEGF is not limited to these. The concentration of VEGF is especially preferably 10 ng/ml.

The concentration of IL-6 in the medium for each of the steps (iii) and (iv) is preferably 1 ng/ml to 100 ng/ml, for example, 1 ng/ml, 5 ng/ml, 10 ng/ml, 20 ng/ml, 30 ng/ml, 40 ng/ml, 50 ng/ml, 75 ng/ml, or 100 ng/ml, but the concentration of IL-6 is not limited to these. The concentration of IL-6 is especially preferably 10 ng/ml.

The concentration of IL-3 in the medium for each of the steps (iii) and (iv) is preferably 1 ng/ml to 100 ng/ml, for example, 1 ng/ml, 5 ng/ml, 10 ng/ml, 20 ng/ml, 30 ng/ml, 40 ng/ml, 50 ng/ml, 75 ng/ml, or 100 ng/ml, but the concentration of IL-3 is not limited to these. The concentration of IL-3 is especially preferably 40 ng/ml.

The concentration of IL-11 in the medium for each of the steps (iii) and (iv) is preferably 500 pg/ml to 50 ng/ml, for example, 500 pg/ml, 750 pg/ml, 1 ng/ml, 5 ng/ml, 10 ng/ml, 20 ng/ml, 30 ng/ml, 40 ng/ml, or 50 ng/ml, but the concentration of IL-11 is not limited to these. The concentration of IL-11 is especially preferably 5 ng/ml.

The concentration of SCF in the medium for each of the steps (iii) and (iv) is preferably 1 ng/ml to 500 ng/ml, for example, 1 ng/ml, 25 ng/ml, 50 ng/ml, 75 ng/ml, 100 ng/ml, 200 ng/ml, 300 ng/ml, 400 ng/ml, or 500 ng/ml, but the concentration of SCF is not limited to these. The concentration of SCF is especially preferably 100 ng/ml.

The concentration of FLT3L in the medium for each of the steps (iii) and (iv) is preferably 1 ng/ml to 500 ng/ml, for example, 1 ng/ml, 25 ng/ml, 50 ng/ml, 75 ng/ml, 100 ng/ml, 200 ng/ml, 300 ng/ml, 400 ng/ml, or 500 ng/ml, but the concentration of FLT3L is not limited to these. The concentration of FLT3L is especially preferably 100 ng/ml.

The concentration of EPO in the medium for the step (iv) is preferably 1 U/ml to 10 U/ml, for example, 1 U/ml, 2 U/ml, 3 U/ml, 4 U/ml, 5 U/ml, 6 U/ml, 7 U/ml, 8 U/ml, 9 U/ml, or 10 U/ml, but the concentration of EPO is not limited to these. The concentration of EPO is especially preferably 4 U/ml.

The concentration of TPO in the medium for the step (iv) is preferably 1 ng/ml to 100 ng/ml, for example, 1 ng/ml, 5 ng/ml, 10 ng/ml, 20 ng/ml, 30 ng/ml, 40 ng/ml, 50 ng/ml, 75 ng/ml, or 100 ng/ml, but the concentration of TPO is not limited to these. The concentration of TPO is especially preferably 50 ng/ml.

The culture period in the Step (i) is preferably not more than 5 days, preferably 1 to 3 days, especially preferably 1 day.

The culture period in the Step (ii) is preferably not more than 10 days, preferably 1 to 5 days, especially preferably 3 days.

The culture period in the Step (iii) is preferably not more than 10 days, preferably 2 to 6 days, especially preferably 4 days.

The culture period in the Step (iv) is preferably not more than 20 days, preferably 5 to 15 days, especially preferably 12 days.

In the present invention, IGF2 is added to the culture medium in order to promote induction of differentiation into hematopoietic stem cells and/or hematopoietic progenitor cells. In the Steps (i) to (iv), IGF2 may be added throughout all steps, or may be added in a specific step(s). For example, IGF2 may be added in the following step(s).

(1) Step (i);
(2) Step (i) and Step (ii);
(3) Step (i) to Step (iii);
(4) Step (i) to Step (iv);
(5) Step (i) and Step (iii);
(6) Step (i), Step (iii), and Step (iv);
(7) Step (i) and Step (iv);
(8) Step (i), Step (ii), and Step (iv);
(9) Step (ii);
(10) Step (ii) and Step (iii);
(11) Step (ii) to Step (iv);
(12) Step (ii) and Step (iv);
(13) Step (iii); or
(14) Step (iii) and Step (iv).

In the Steps (i) to (iv), the concentration of IGF2 added may be the same throughout all steps, or may be different among the steps. The concentration of IGF2 added in each of the steps (i) to (iv) is preferably 1 ng/ml to 500 ng/ml, for example, 1 ng/ml, 25 ng/ml, 50 ng/ml, 75 ng/ml, 100 ng/ml, 200 ng/ml, 300 ng/ml, 400 ng/ml, or 500 ng/ml, but the concentration of IGF2 is not limited to these.

A step of extraction/purification of mesodermal cells may be included after the production step (ii). Any method may be used for the extraction/purification of mesodermal cells as long as mesodermal cells can be separated with high purity from a cell population containing mesodermal cells. For example, the method may be extraction/purification by flow cytometry. In the present invention, the cells may be further selected using as an index SSEA-1 negativity (that is, SSEA-1$^-$) so that undifferentiated cells are not contained in the extracted/purified mesodermal population. Selection of Flk1-positive (that is, Flk1$^+$) cells and SSEA-1$^-$ cells may be carried out at the same time, or as separate steps. For example, selection of Flk1$^+$/SSEA-1$^-$ cells may be carried out at the same time using flow cytometry.

In the present process, the culture temperature is about 30 to 40° C., preferably about 37° C., although the culture temperature is not limited thereto. The culture is carried out under an atmosphere of $CO_2$-containing air. The $CO_2$ concentration is about 2 to 5%, preferably 5%. This step may also be carried out under low oxygen conditions, and, in such a case, the oxygen concentration is 1 to 10%, preferably 5%, although the oxygen concentration is not limited thereto.

In the present process, the medium may further contain a ROCK inhibitor. In particular, in cases where the process includes a step of dispersing human pluripotent stem cells into single cells, the medium preferably contains a ROCK inhibitor. The ROCK inhibitor is not limited as long as it can suppress the function of Rho kinase (ROCK). Examples of ROCK inhibitors that may be used in the present invention include Y-27632.

Method for Selecting Cells Showing High Efficiency of Differentiation into Hematopoietic Stem Cells and/or Hematopoietic Progenitor Cells In the present invention, cells showing high efficiency of differentiation into hematopoietic stem cells and/or hematopoietic progenitor cells can be specifically selected using, as an index/indices, high expression and/or low expression of one or more genes selected from the group consisting of IGF2, T, HOXB4, GATA2, CEBPA, MESP1, CDX2, BMP4, EOMES, SOX17, GATA6, GATA4, and SNAI2 in iPS cells established as described above.

The term "cells showing high efficiency of differentiation into hematopoietic stem cells and/or hematopoietic progenitor cells" means cells having relatively high tendency of differentiation into hematopoietic stem cells and/or hematopoietic progenitor cells, and showing high expression of a gene(s) important for differentiation into mesoderm and/or gene(s) important for differentiation into hematopoietic stem cells. The "cells showing high efficiency of differentiation into hematopoietic stem cells and/or hematopoietic progenitor cells" may be, for example, cells from which an equivalent or larger number of hematopoietic stem cells and/or hematopoietic progenitor cells are induced relative to those induced from 585A1, H9, TIG1204F1, KRV-1, khES3, 7-KE2, TIG1074F1, 201B6, 454E2, 610B1, 665A7, or 253G4, when differentiation induction into hematopoietic lineage cells is carried out by an ordinary method in the art. On the other hand, the term "cells showing low efficiency of differentiation into hematopoietic stem cells and/or hematopoietic progenitor cells" as used in the present specification means cells having relatively low tendency of differentiation into hematopoietic stem cells and/or hematopoietic progenitor cells, and showing low expression of a gene(s) important for differentiation into mesoderm and/or gene(s) important for differentiation into hematopoietic stem cells. The "cells showing low efficiency of differentiation into hematopoietic stem cells and/or hematopoietic progenitor cells" may be, for example, cells from which an equivalent or smaller number of hematopoietic stem cells and/or hematopoietic progenitor cells are induced relative to those induced from 589B1, 648B1, 751A3, 451F3, 427F1, 609A1, 744A2, 751B4, 783F1, 784D1, 246G1, or 588A4, when differentiation induction into hematopoietic lineage cells is carried out by an ordinary method in the art.

Examples of the genes important for differentiation into mesoderm include, but are not limited to, IGF2, GATA6, GATA4, SNAI2, MESP1, T, EOMES, SOX17, BMP4, CDX2, MESP2, and SNAIL. Examples of the genes important for differentiation into hematopoietic stem cells include, but are not limited to, GATA2, HOXB4, CEBPA, and RUNX1.

The sequence information on the respective genes derived from human or mouse can be obtained by reference to the NCBI (USA) accession numbers listed in Table 1.

TABLE 1

Genes which may be used as indices

| Gene name | NCBI Accession NO. | |
|---|---|---|
| | Mouse | Human |
| IGF2 | NM_010514 | NM_000612 |
| T (Brachyury) | NM_009309 | NM_003181 |
| HOXB4 | NM_010459 | NM_024015 |
| GATA2 | NM_008090 | NM_001145661 |
| CEBPA | NM_007678 | NM_004364 |
| MESP1 | NM_008588 | NM_018670 |
| CDX2 | NM_007673 | NM_001265 |
| BMP4 | NM_007554 | NM_001202 |
| EOMES | NM_010136 | NM_005442 |
| SOX17 | NM_011441 | NM_022454 |
| GATA6 | NM_010258 | NM_005257 |
| GATA4 | NM_008092 | NM_002052 |
| SNAI2 | NM_011415 | NM_003068 |

The method for detecting the genes is not limited, and examples of the method include hybridization such as Northern blotting and in situ hybridization; RNase protection assay; PCR; real-time PCR; and microarray analysis.

A preferred detection method may be carried out by extracting total RNA containing mRNA from a biological sample; obtaining the mRNA using a poly (T) column; synthesizing cDNA by reverse transcription; amplifying the synthesized cDNA using a phage or by a PCR cloning method; and then, for example, carrying out hybridization using a probe complementary to the target DNA, which probe has a size of about 20-mer to 70-mer or has a size larger than this, or carrying out quantitative PCR using a primer with a size of about 20-mer to 30-mer. As a label for the hybridization or PCR, a fluorescent label may be used. Examples of fluorescent labels that may be used include cyanine, fluorescamine, rhodamine, and derivatives thereof, such as Cy3, Cy5, FITC, and TRITC.

In the selection of iPS cells showing high efficiency of differentiation into hematopoietic stem cells and/or hematopoietic progenitor cells, the expression level(s) of one or more genes selected from the group consisting of IGF2, T, HOXB4, GATA2, CEBPA, MESP1, CDX2, BMP4, EOMES, SOX17, GATA6, GATA4, and SNAI2 detected by a method described above in iPS cells or embryonic stem cells (ES cells) which are known to show high efficiency of differentiation into hematopoietic stem cells and/or hematopoietic progenitor cells may be set as a reference value(s) (positive reference value(s)), and subject iPS cells showing a value(s) equivalent to or higher than the reference value(s) may be selected as iPS cells showing high efficiency of differentiation into hematopoietic stem cells and/or hematopoietic progenitor cells.

Similarly, the expression level(s) of one or more genes selected from the group consisting of IGF2, T, HOXB4, GATA2, CEBPA, MESP1, CDX2, BMP4, EOMES, SOX17, GATA6, GATA4, and SNAI2 detected by a method described above in iPS cells or embryonic stem cells (ES cells) which are known to show low efficiency of differentiation into hematopoietic stem cells and/or hematopoietic progenitor cells may be set as a reference value(s) (negative reference value(s)), and subject iPS cells showing a value(s) higher than the reference value(s) may be selected as iPS cells showing high efficiency of differentiation into hematopoietic stem cells and/or hematopoietic progenitor cells.

Alternatively, iPS cells showing high efficiency of differentiation into hematopoietic stem cells and/or hematopoietic progenitor cells may be selected by setting, as a reference value(s) (negative reference value(s)), the expression level(s) of one or more genes selected from the group consisting of IGF2, T, HOXB4, GATA2, CEBPA, MESP1, CDX2, BMP4, EOMES, SOX17, GATA6, GATA4, and SNAI2 detected by a method described above in iPS cells or embryonic stem cells (ES cells) which are known to show high efficiency of differentiation into hematopoietic stem cells and/or hematopoietic progenitor cells, and excluding subject iPS cells showing a value(s) lower than the reference value(s) as iPS cells showing low efficiency of differentiation into hematopoietic stem cells and/or hematopoietic progenitor cells.

Alternatively, iPS cells showing high efficiency of differentiation into hematopoietic stem cells and/or hematopoietic progenitor cells may be selected by setting, as a reference value(s) (positive reference value(s)), the expression level(s) of one or more genes selected from the group consisting of IGF2, T, HOXB4, GATA2, CEBPA, MESP1, CDX2, BMP4, EOMES, SOX17, GATA6, GATA4, and SNAI2 detected by a method described above in iPS cells or embryonic stem cells (ES cells) which are known to show low efficiency of differentiation into hematopoietic stem cells and/or hematopoietic progenitor cells, and excluding subject iPS cells showing a value(s) equivalent to or lower than the reference value(s) as iPS cells showing low efficiency of differentiation into hematopoietic stem cells and/or hematopoietic progenitor cells.

Method for Selecting Cells Having High Capacity to Differentiate into Blood Cells In the present invention, cells showing high efficiency of differentiation into blood cells can be specifically selected using, as an index/indices, high expression and/or low expression of one or more genes selected from the group consisting of TRIM58, CTSF, FAM19A5, and TCERG1L, or low DNA methylation and/or high DNA methylation of the TRIM58, CSMD1, and/or FAM19A5 gene(s), in iPS cells established as described above.

The term "cells having high capacity to differentiate into blood cells" as used herein means cells having relatively high tendency of differentiation into blood cells. The term "having high capacity to differentiate into blood cells" means, for example, that one or more colonies can be formed in a colony formation assay. The "cells having high capacity to differentiate into blood cells" may be, for example, cells capable of forming an equivalent or larger number of colonies compared to 751A3, 783F1, 751B4, 692D2, 783A2, 744A2, 744B9, 609A2, 585B1, 784D1, 609A1, 648B1, 665A7, 451F3, 610B1, 606A1, 648A1, or khES3 in a colony formation assay. Examples of the "cells which are known to have high capacity to differentiate into blood cells" include, but are not limited to, 751A3, 783F1, 751B4, 692D2, 783A2, 744A2, 744B9, 609A2, 585B1, 784D1, 609A1, 648B1, 665A7, 451F3, 610B1, 606A1, 648A1, and/or khES3. On the other hand, the term "cells having low capacity to differentiate into blood cells" as used in the present description means cells having relatively low tendency of differentiation into blood cells. The term "having low capacity to differentiate into blood cells" means, for example, that colonies cannot be formed in a colony formation assay, or that the cells are in a state which is substantially the same as this state. The "cells having low capacity to differentiate into blood cells" maybe, for example, cells that form an equivalent or smaller number of colonies compared to 427F1, khES1, TIG1204F1, H9, Kept, 454E2, 253G1, KRV-1, 457C1, 7-KE2, 201B7, TIG1074F1, 246G1, 409B2, 201B6, 253G4, 404C2, or 588A4 in a colony formation assay. Examples of the "cells which are known to have low capacity to differentiate into blood cells" include, but are not limited to, 427F1, khES1, TIG1204F1, H9, Kept, 454E2, 253G1, KRV-1, 457C1, 7-KE2, 201B7, TIG1074F1, 246G1, 409B2, 201B6, 253G4, 404C2, and/or 588A4.

In the present invention, the term "blood cells" means a cell component(s) present in blood, and may be one or more kinds of cells selected from the group consisting of erythrocytes, platelets, monocytes, T cells, B cells, NK cells, neutrophils, eosinophils, basophils, granulocytes, and macrophages, but the "blood cells" are not limited to these. The "blood cells" may be preferably cells that develop in a colony assay, for example, erythrocytes, granulocytes, and/or macrophages.

The sequence information on the respective genes derived from human or mouse can be obtained by reference to the NCBI (USA) accession numbers listed in Table 2. However, their sequences are not limited to these since gene sequences may have variations among, for example, different species.

TABLE 2

Genes which may be used as indices

| Gene name | NCBI Accession NO. | |
|---|---|---|
| | Mouse | Human |
| TRIM58 | NM_001039047 | NM_015431 (SEQ ID NO: 1) |
| CTSF | NM_019861 | NM_003793 (SEQ ID NO: 2) |
| FAM19A5 | NM_134096 | NM_001082967 (SEQ ID NO: 3) |
| TCERG1L | NM_183289 | NM_174937 (SEQ ID NO: 4) |
| CSMD1 | NM_053171 | NM_033225 (SEQ ID NO: 5) |

The method for detecting the genes is not limited, and examples of the method include hybridization such as Northern blotting and in situ hybridization; RNase protection assay; PCR; real-time PCR; and microarray analysis.

A preferred detection method may be carried out by extracting total RNA containing mRNA from a biological sample; obtaining the mRNA using a poly (T) column; synthesizing cDNA by reverse transcription; amplifying the synthesized cDNA using a phage or by a PCR cloning method; and then, for example, carrying out hybridization using a probe complementary to the target DNA, which probe has a size of about 20-mer to 70-mer or has a size larger than this, or carrying out quantitative PCR using a primer with a size of about 20-mer to 30-mer. As a label for the hybridization or PCR, a fluorescent label may be used. Examples of fluorescent labels that may be used include cyanine, fluorescamine, rhodamine, and derivatives thereof, such as Cy3, Cy5, FITC, and TRITC.

In the selection of iPS cells having high capacity to differentiate into blood cells, the expression level(s) of one or more genes selected from the group consisting of TRIM58, CTSF, FAM19A5, and TCERG1L detected by a method described above in iPS cells or embryonic stem cells (ES cells) which are known to have high capacity to differentiate into blood cells may be set as a reference value(s), and subject iPS cells showing a value(s) equivalent to or higher than the reference value(s) (positive reference value(s)) may be selected as iPS cells having high capacity to differentiate into blood cells.

Similarly, the expression level(s) of one or more genes selected from the group consisting of TRIM58, CTSF, FAM19A5, and TCERG1L detected by a method described above in iPS cells or embryonic stem cells (ES cells) which are known to show low capacity to differentiate into blood cells may be set as a reference value(s) (negative reference value(s)), and subject iPS cells showing a value(s) higher than the reference value(s) may be selected as iPS cells having high capacity to differentiate into blood cells.

Alternatively, iPS cells having high capacity to differentiate into blood cells may be selected by setting, as a reference value(s) (negative reference value(s)), the expression level(s) of one or more genes selected from the group consisting of TRIM58, CTSF, FAM19A5, and TCERG1L detected by a method described above in iPS cells or embryonic stem cells (ES cells) which are known to have high capacity to differentiate into blood cells, and excluding subject iPS cells showing a value(s) lower than the reference value(s) as iPS cells having low capacity to differentiate into blood cells.

Alternatively, iPS cells having high capacity to differentiate into blood cells may be selected by setting, as a reference value(s) (positive reference value(s)), the expression level(s) of one or more genes selected from the group consisting of TRIM58, CTSF, FAM19A5, and TCERG1L detected by a method described above in iPS cells or embryonic stem cells (ES cells) which are known to have low capacity to differentiate into blood cells, and excluding subject iPS cells showing a value(s) equivalent to or lower than the reference value(s) as iPS cells having low capacity to differentiate into blood cells.

Further, in the present invention, iPS cells having high capacity to differentiate into blood cells may be selected by measuring the methylation state of DNA involved in regulation of gene expression in the TRIM58, CSMD1, and/or FAM19A5 gene region(s).

As a method for measuring the DNA methylation state, a known methylation analysis method may be used. For example, a method in which unmethylated recognition sequences are cleaved with a restriction enzyme is known. When DNA is treated with a methylation-sensitive restriction enzyme, unmethylated recognition sites are cleaved. By subjecting the resulting DNA to electrophoresis and carrying out Southern blotting or the like, the presence or absence of methylation in a region of interest can be judged based on differences in the lengths of detected bands.

Examples of the methylation-sensitive restriction enzyme include SmaI and HpaII, and the methylation-sensitive restriction enzyme is preferably SmaI. Those skilled in the art can easily know methylation-insensitive restriction enzymes that recognize the same recognition sequences as those of methylation-sensitive restriction enzymes, and these methylation-insensitive restriction enzymes may be used in combination with the methylation-sensitive restriction enzymes.

In another method for measuring the DNA methylation state, bisulfite may be used. When DNA is treated with bisulfite, only unmethylated cytosine is converted to uracil, while methylated cytosine is left unconverted as cytosine. In bisulfite sequencing, a bisulfite-treated genomic region is amplified by PCR, cloned, and then sequenced to investigate the presence or absence of DNA methylation. The presence or absence of DNA methylation may also be detected by COBRA (Combined bisulfite restriction analysis), in which bisulfite-treated DNA is cleaved with a restriction enzyme, and the presence or absence of a remaining restriction enzyme recognition site(s) is investigated. Methylation-specific PCR may also be used. In this method, PCR primers are made to recognize a difference(s) between the sequences before and after the bisulfite treatment, and the presence or absence of methylated DNA or unmethylated DNA is judged based on the presence or absence of a PCR product(s). Alternatively, methylation-specific oligonucleotide (MSO) microarray; or Chromatin Immuno-Precipitation (ChIP), in which the DNA sequence of a methylated DNA region is extracted using a DNA methylation-specific antibody, and PCR and sequencing are carried out to detect the DNA methylation state of a specific region; may be used.

In the selection of iPS cells having high capacity to differentiate into blood cells, the DNA methylation level(s) of the TRIM58, CSMD1, and/or FAM19A5 gene region(s) detected by a method described above in both chromosomes in iPS cells or embryonic stem cells (ES cells) which are known to have high capacity to differentiate into blood cells may be set as a reference value(s) (positive reference value(s)), and subject iPS cells showing a value(s) equivalent to or lower than the reference value(s) may be selected as iPS cells having high capacity to differentiate into blood cells.

Similarly, the DNA methylation level(s) of the TRIM58, CSMD1, and/or FAM19A5 gene region(s) detected by a method described above in both chromosomes in iPS cells or embryonic stem cells (ES cells) which are known to have low capacity to differentiate into blood cells may be set as a reference value(s) (negative reference value(s)), and subject iPS cells showing a value(s) lower than the reference value(s) may be selected as iPS cells having high capacity to differentiate into blood cells.

Alternatively, iPS cells having high capacity to differentiate into blood cells may be selected by setting, as a reference value(s) (negative reference value(s)), the DNA methylation level(s) of the TRIM58, CSMD1, and/or FAM19A5 gene region(s) detected by a method described above in both chromosomes in iPS cells or embryonic stem cells (ES cells) which are known to have high capacity to differentiate into blood cells, and excluding subject iPS cells showing a value(s) higher than the reference value(s) as iPS cells having low capacity to differentiate into blood cells.

Alternatively, iPS cells having high capacity to differentiate into blood cells may be selected by setting, as a reference value(s) (positive reference value(s)), the DNA methylation level(s) of the TRIM58, CSMD1, and/or FAM19A5 gene region(s) detected by a method described above in both chromosomes in iPS cells or embryonic stem cells (ES cells) which are known to have low capacity to differentiate into blood cells, and excluding subject iPS cells showing a value(s) equivalent to or higher than the reference value(s) as iPS cells having low capacity to differentiate into blood cells.

In terms of the method for detecting the ratio of methylated DNA in cases where unmethylated recognition sequences are cleaved with a restriction enzyme, the ratio can be calculated by fragmenting DNA and quantifying the DNA by Southern blotting, followed by comparing the amount of DNA which is not fragmented and the amount of DNA which is fragmented. On the other hand, in the cases of bisulfite sequencing, arbitrarily selected chromosomes are sequenced. Therefore, templates prepared by cloning of PCR products are repeatedly sequenced a plurality of times, for example, not less than 2 times, preferably not less than 5 times, more preferably not less than 10 times. By comparing the number of clones in which DNA methylation is detected and the number of clones sequenced, the ratio of methylated DNA can be calculated. In cases where pyrosequencing is used, direct measurement is possible based on the ratio between cytosine and thymine. In cases where chromatin immuno-precipitation (ChIP) is carried out using a DNA methylation-specific antibody, the amount of DNA of interest precipitated and the amount of the DNA before the precipitation are detected by PCR, and then compared. By this, the ratio of DNA methylation can be detected.

Kit for Selecting Cells Showing High Efficiency of Differentiation into Hematopoietic Stem Cells and/or Hematopoietic Progenitor Cells The present invention provides a kit which is useful for selecting pluripotent stem cells, preferably induced pluripotent stem cells, showing high efficiency of differentiation into hematopoietic stem cells and/or hematopoietic progenitor cells. Examples of the kit for selecting the cells showing high efficiency of differentiation into hematopoietic stem cells and/or hematopoietic progenitor cells according to the present invention include, but are not limited to, gene assay kits, microarrays, and DNA methylation assay kits based on the measurement methods described above.

In the present invention, the target gene(s) to be assayed may be one or more genes selected from the group consisting of, for example, IGF2, T, HOXB4, GATA2, CEBPA, MESP1, CDX2, BMP4, EOMES, SOX17, GATA6, GATA4, and SNAI2. The target gene to be assayed is preferably the IGF2 gene.

The gene assay kit may contain a nucleic acid or artificial nucleic acid probe complementary to the target DNA or mRNA of the gene, which probe has a size of about 20-mer to 70-mer or has a size larger than this, or may contain a primer having a size of about 20-mer to 30-mer.

The artificial nucleic acid probe may contain a modified base (e.g., conversion of adenine, cytosine, guanine, or thymine to a modified base such as inosine, 5-methylcytosine, 2-aminopurine, 2-amino-6-chloropurine, or 2,6-diaminopurine), conversion of a phosphodiester bond to a phosphorothioate bond, conversion of the 2'-hydroxyl group of a ribose to a 2'-O-methyl group or 2'-O-methoxyethyl group, LNA (Locked Nucleic Acid) or BNA (Bridged Nucleic Acid) having a structure in which the 2'-position and the 4'-position of a ribose are cross-linked through a methylene group, PNA (Peptide Nucleic Acid) whose backbone is composed of peptide bonds of N-(2-aminoethyl)glycine, and/or the like (e.g., A. A. Koshikin et al., Tetrahedron 54: 3607 (1998); S. Obika et al., Tetrahedron Lett. 39: 5401 (1998); P. E. Nielson et al., Science 254: 1497 (1991); JP 2010-150280 A; and JP 2010-090159 A).

The kit for selecting an iPS cell(s) according to the present invention may contain a microarray prepared by binding these probes to a carrier(s).

This kit may further contain, for example, a reagent for extraction of one or more genes selected from the group consisting of IGF2, T, HOXB4, GATA2, CEBPA, MESP1, CDX2, BMP4, EOMES, SOX17, GATA6, GATA4, and SNAI2; gene extraction reagent; and/or chromosome extraction reagent.

The kit of the present invention may also be used for diagnosis. The diagnosis kit of the present invention may contain a means for a discriminant analysis, such as a document or instruction describing a procedure of the discriminant analysis, a program for carrying out the procedure of the discriminant analysis in a computer, a program list thereof, a computer-readable recording medium in which the program is recorded (e.g., flexible disk, optical disk, CD-ROM, CD-R, or CD-RW), and/or a device or system with which the discriminant analysis is carried out (e.g., computer).

Kit for Selecting Cells Having High Capacity to Differentiate into Blood Cells

The present invention provides a kit useful for selecting induced pluripotent stem cell having high capacity to differentiate into blood cells. Examples of the kit for selecting cells having high capacity to differentiate into blood cells according to the present invention include, but are not limited to, gene assay kits, microarrays, and DNA methylation assay kits based on the measurement methods described above.

In the present invention, the target gene to be assayed may be one or more genes selected from the group consisting of, for example, the TRIM58, CTSF, FAM19A5, and TCERG1L genes. The target gene to be assayed is preferably the TRIM58 gene.

The gene assay kit may contain a nucleic acid or artificial nucleic acid probe complementary to the target DNA or mRNA of the gene, which probe has a size of about 20-mer to 70-mer or has a size larger than this, or may contain a primer having a size of about 20-mer to 30-mer.

The artificial nucleic acid probe may contain a modified base (e.g., conversion of adenine, cytosine, guanine, or thymine to a modified base such as inosine, 5-methylcytosine, 2-aminopurine, 2-amino-6-chloropurine, or 2,6-diaminopurine), conversion of a phosphodiester bond to a phosphorothioate bond, conversion of the 2'-hydroxyl group of a ribose to a 2'-O-methyl group or 2'-O-methoxyethyl group, LNA (Locked Nucleic Acid) or BNA (Bridged Nucleic Acid) having a structure in which the 2'-position and the 4'-position of a ribose are cross-linked through a methylene group, PNA (Peptide Nucleic Acid) whose backbone is composed of peptide bonds of N-(2-aminoethyl)glycine, and/or the like (e.g., A. A. Koshikin et al., Tetrahedron 54: 3607 (1998); S. Obika et al., Tetrahedron Lett. 39: 5401 (1998); P. E. Nielson et al., Science 254: 1497 (1991); JP 2010-150280 A; and JP 2010-090159 A).

The kit for selecting iPS cells according to the present invention may contain a microarray prepared by binding these probes to a carrier(s).

The DNA methylation assay kit may contain a methylation-sensitive and/or methylation-insensitive restriction enzyme(s). In cases where DNA is treated with a methylation-sensitive restriction enzyme, unmethylated recognition sites are cleaved. By subjecting the resulting DNA to electrophoresis and carrying out Southern blotting or the like, the presence or absence of methylation in a region of interest can be judged based on differences in the lengths of detected bands.

The kit may also contain a bisulfite reagent for detecting methylation of cytosine bases utilizing the bisulfite reaction. The kit may also contain a reagent and/or microarray to be used for MSO (methylation-specific oligonucleotide) microarray analysis utilizing the bisulfite reaction (Izuho Hatada, Experimental Medicine, Vol. 24, No. 8 (extra edition), pp. 212-219 (2006).

Irrespective of whether the bisulfite treatment is carried out or not, the kit may also contain a probe(s) and/or primer(s) specific to a target region(s) (for example, a region(s) regulating expression of the TRIM58, CSMD1, and/or FAM19A5 gene(s)). In the methylation-specific oligonucleotide (MSO) microarray analysis, bisulfite-treated DNA is subjected to PCR using, as primers, sequences which do not change due to methylation (that is, a sequence containing no CpG sequence). As a result, unmethylated cytosine is amplified as thymine, and methylated cytosine is amplified as cytosine.

The DNA methylation assay kit may also contain a reagent for amplification of a target region such as a region regulating expression of a gene, and may contain, if necessary, a component(s) required for PCR, such as a DNA polymerase, appropriate buffer, magnesium salt, and/or dNTPs.

The kit for selecting cells having high capacity to differentiate into blood cells of the present invention may also contain, as a negative control(s), methylated DNA of a target region(s) such as a region(s) regulating expression of the TRIM58, CSMD1, and/or FAM19A5 gene(s) in cells having low capacity to differentiate into blood cells. The kit may also contain, as a positive control(s), unmethylated DNA of a target region(s) such as a region(s) regulating expression of the TRIM58, CSMD1, and/or FAM19A5 gene(s) in cells having high capacity to differentiate into blood cells.

This kit may further contain, for example, a reagent for extraction of one or more genes selected from the group consisting of the TRIM58, CTSF, FAM19A5, and TCERG1L genes; gene extraction reagent; and/or chromosome extraction reagent. Alternatively, the kit may contain a reagent for extraction of the TRIM58, CSMD1, and/or FAM19A5 gene(s); gene extraction reagent; and/or chromosome extraction reagent.

The kit of the present invention may also be used for diagnosis. The diagnosis kit of the present invention may contain a means for a discriminant analysis, such as a document or instruction describing a procedure of the discriminant analysis, a program for carrying out the procedure of the discriminant analysis in a computer, a program list thereof, a computer-readable recording medium in which the program is recorded (e.g., flexible disk, optical disk, CD- ROM, CD-R, or CD-RW), and/or a device or system with which the discriminant analysis is carried out (e.g., computer).

EXAMPLES

The present invention is described below more concretely by way of Examples. Needless to say, however, the present invention is not limited to these.

Example 1

Cells

As human ES cells, KhES1 and KhES3 (Suemori H, et al. Biochem Biophys Res Commun. 345: 926-32, 2006), and H1 and H9 (Thomson, J. A., et al., Science 282: 1145-1147, 1998) were used. As iPS cells, the cells shown below in Table 3 were used.

Biotechnol 26 (1), 101, 2008; Aoi, T. et al., Science 321, 699-702, 2008; and Okita K, et al., Science 322, 949, 2008).

Example 2

Effect of IGF2 on Differentiation into Hematopoietic Progenitor Cells

In order to investigate the effect of IGF2 on induction of differentiation of human iPS cells into hematopoietic progenitor cells, an experiment of induction of differentiation into hematopoietic progenitor cells was carried out. Briefly, the induction of differentiation into hematopoietic progenitor cells was carried out according to the following procedure.

(Day 0 to Day 1)

The obtained iPS cells were subjected to culture of small clusters (10 to 20 cells) of iPS cells containing no feeder cells for 24 hours using a 6-well low-cluster plate (Corning

TABLE 3 iPS cells used

| C bne Name | Method | feeder | Origin | Factors | Reference |
|---|---|---|---|---|---|
| 585A1 | Episomalplasmid | SNL | PBMN #1 abT | OSKUL + shp53 | Okita et al, Stem Cells. 31(3):458-66 (2013) |
| TIG1204F1 | Retrovirus | SNL | TIG120 | OSKM | Takahashi et al, unpub lished |
| KR V-1 | Retrovirus | SNL | Keratinocyte#1 | OSKM | Yokota et al, unpublished |
| 7-KE2 | Retrovirus | SNL | Keratinocyte#2 | OSKM | Tanabe et al, unpublished |
| TIG1074F1 | Retrovirus | SNL | TIG107 | OSKM | Takahashi et al, unpublished |
| 201B6 | Retrovirus | SNL | HDF1388 | OSKM | Takahashi et al, Cell 131,861-72.(2007) |
| 454E2 | Episomalplasmid | SNL | DP74 | OSKUL + shp53 | Okita et al, Nat Methods. 8 (5):409-12.(2011) |
| 610B1 | Episomalplasmid | SNL | CBCD34#2 | OSKUL + shp53 | Okita et al, Stem Cells. 31(3):458-66 (2013) |
| 665A7 | Sendaivirus | SNL | CBCD34#2 | OSKM | Okita et al, unpublished |
| 253G4 | Retrovirus | SNL | HDF1388 | OSK | Nakagawa et al, Nat Biotechnol 26(1):101-6. (2008) |
| 457C1 | Episomalplasmid | SNL | DP74 | OSKUL + shp53 | Okita et al, NatMethods. 8(5):409-12.(2011) |
| 692D2 | Episomalplasmid | SNL | PBMN #1 abT | OSKUL + shp53 | Okita et al, Stem Cells. 31(3):458-66 (2013) |
| 201B7 | Retrovirus | SNL | HDF1388 | OSKM | Takahashi et al, Cell 131,861-72. (2007) |
| 585B1 | Episomalplasmid | SNL | PBMN #1 abT | OSKUL + shp53 | Okita et al, Stem Cells. 31(3):458-66 (2013) |
| 744B9 | Episomalplasmid | SNL | SF91-PBMN, abT | OSKUL + shp53 | Kajiwara et al, Proc Natl Acad Sci U S A. 109(31):12538-43 (2012) |
| 404C2 | Episomalplasmid | SNL | HDF1388 | OSKUL + shp53 | Okita et al, Nat Methods. 8(5):409-12. (2011) |
| 409B2 | Episomalplasmid | SNL | HDF1388 | OSKUL + shp53 | Okita et al, Nat Methods. 8(5):409-12. (2011) |
| 609A2 | Episomalplasmid | SNL | HDF-PD12 | OSKUL + shp53 | Kajiwara et al, Proc Natl Acad Sci U S A. 109(31):12538-43 (2012) |
| 606A1 | Episomalplasmid | SNL | CB CD34#1 | OSKUL + shp53 | Okita et al, Stem Cells. 31(3):458-66 (2013) |
| 253G1 | Retrovirus | SNL | HDF1388 | OSK | Nakagawa et al, Nat Biotechnol 26(1):101-6. (2008) |
| 648A1 | Episomalplasmid | SNL | PBMN #2 non-T, non-B | OSKUL + shp53 | Okita et al, Stem Cells. 31(3):458-66 (2013) |
| 783A2 | Episomalplasmid | SNL | PD12 PBMN non-T, non-B | OSKUL + shp53 | Kajiwara et al, Proc NatlAcad SciU S A. 109 (31)12538-43 (2012) |
| Kep1 | Episomalplasmid | SNL | Keratinocyte#1 | OSKUL + shp53 | Yokota et al, unpublished |
| 589B1 | Episomalplasmid | SNL | HDF-PD12 | OSKUL + shp53 | Okita et al, unpublished |
| 648B1 | Episomalplasmid | SNL | PBIT BBB non-T,non-B | OSKUL + shp53 | Okita et al, Stem Cells. 31(3):458-66 (2013) |
| 751A3 | Episomalplasmid | SNL | HDF-SF91 | OSKUL + shp53 | Kajiwara et al, Proc Natl Acad Sci U S A. 109(31):12538-43 (2012) |
| 451F3 | Episomalplasmid | SNL | DP74 | OSKUL + shp53 | Okita et al, Nat Methods. 8 (5) 409-12. (2011) |
| 427F1 | Episomalplasmid | SNL | HDF-1437 | OSKUL + shp53 | Okita et al, unpublished |
| 609A1 | Episomalplasmid | SNL | HDF-PD12 | OSKUL + shp53 | Kajiwara et al, Proc Natl Acad Sci U S A. 109(31):12538-43 (2012) |
| 744A2 | Episomalplasmid | SNL | SF91-PBMN, abT | OSKUL + shp53 | Kajisiara et al, Proc Natl Acad Sci U S A. 109(31):12538-43 (2012) |
| 751B4 | Episomalplasmid | SNL | HDF-SF91 | OSKUL + shp53 | Kajiwara et al, Proc Natl Acad Sci U S A. 109(31):12538-43 (2012) |
| 783F1 | Episomalplasmid | SNL | PD12PBMN, abT | OSKUL + shp53 | Okita et al, unpublished |
| 784D1 | Episomalplasmid | SNL | PD15PBMN, abT | OSKUL + shp53 | Kajiwara et al, Proc Natl Acad Sci U S A. 109(31):12538-43 (2012) |
| 246G1 | Retrovirus | SNL | BJ | OSKM | Takahashi et al, C el1131,861-72. (2007) |
| 588A4 | Episomalplasmid | SNL | HDF-PD15 | O SKUL + shp53 | Kajiwara et al, Proc Natl Acad Sci U S A. 109(31):12538-43 (2012) |

Culture of ES cells, and establishment and culture of iPS cells were carried out by conventional methods (Takahashi K and Yamanaka S, Cell 126 (4), 663, 2006; Okita K, et al., Nature 448 (7151), 313, 2007; Nakagawa M, et al., Nat Incorporated) under the conditions of 37° C., 5% $CO_2$, 5% $O_2$, and 90% $N_2$ in an aggregation medium composed of StemPro-34 (Invitrogen) supplemented with human bone morphogenetic protein-4 (BMP-4; 10 ng/ml), Y27632 (10

μM), 2 mM glutamine, penicillin/streptomycin, 4×10$^{-4}$ M monothioglycerol (Sigma-Aldrich), and 50 μg/ml ascorbic acid (Sigma-Aldrich), to prepare embryoid bodies (EBs).
(Day 1 to Day 4)
The obtained EBs were collected and washed, followed by performing culture for additional 3 days in StemPro-34 supplemented with 5 ng/ml bFGF, 10 ng/ml BMP-4, 2 mM glutamine, penicillin/streptomycin, 4×10$^{-4}$ M monothioglycerol, and 50 μg/ml ascorbic acid, thereby inducing primitive streak/mesoderm formation.
(Day 4 to Day 8)
On Day 4, EBs were collected again, and then cultured again for 4 days in StemPro-34 supplemented with vascular endothelial growth factor (VEGF; 10 ng/ml), bFGF (1 ng/ml), interleukin-6 (IL-6; 10 ng/ml), IL-3 (40 ng/ml), IL-11 (5 ng/ml), stem cell factor (SCF; 100 ng/ml), and human FLT3 ligand (FLT3L; 100 ng/ml), for specialization and development into hematopoietic progenitor cells.
(Day 8 to Day 15)
On Day 8, EBs were transferred to an environment of 5% $CO_2$/air, and cultured for additional 7 days in StemPro-34 supplemented with VEGF (10 ng/ml), erythropoietin (EPO; 4 U/ml), thrombopoietin (TPO; 50 ng/ml), SCF (100 ng/ml), FLT3L (100 ng/ml), IL-6 (10 ng/ml), IL-11 (5 ng/ml), and IL-3 (40 ng/ml), for maturation (maturation into erythroblasts and megakaryocytic progenitor cells) and expansion into hematopoietic progenitor cells. The cells were then incubated at 37° C. for 5 to 10 minutes with 0.25% Trypsin-EDTA, and dissociated using a 1000-ml pipette to prepare a single-cell suspension. The dissociated cells were passed through a 70-μm filter, and the collected cells were then evaluated by flow cytometry.

Through the above-described steps of (Day 0 to Day 1), (Day 1 to Day 4), (Day 4 to Day 8), and (Day 8 to Day 15), the effect of IGF2 was investigated by addition of IGF2 at various concentrations (20 ng/ml, 50 ng/ml, and 100 ng/ml). In addition to IGF2, an anti-IGF1R antibody was added in order to investigate whether the differentiation-inducing effect on hematopoietic progenitor cells occurred IGF2-specifically.

As a result, IGF2 was found to increase the efficiency of inducing differentiation of human iPS cells into blood in a concentration-dependent manner (FIG. 1(A)). Further, the effect was confirmed to be produced by IGF2 (FIG. 1(B)).

Example 3

Confirmation of Efficiency of Differentiation into Hematopoietic Stem Cells and/or Hematopoietic Progenitor Cells In order to investigate the efficiency of differentiation into hematopoietic stem cells and/or hematopoietic progenitor cells, differentiation of 4 ES cell lines and 35 iPS cell lines into CD43-positive cells was induced using the EB method including the following process.
(Day 0 to Day 1)
The obtained iPS cells were subjected to culture of small clusters (10 to 20 cells) of iPS cells containing no feeder cells for 24 hours using a 6-well low-cluster plate (Corning Incorporated) under the conditions of 37° C., 5% $CO_2$, 5% $O_2$, and 90% $N_2$ in an aggregation medium composed of StemPro-34 (Invitrogen) supplemented with human bone morphogenetic protein-4 (BMP-4; 10 ng/ml), Y27632 (10 μM), 2 mM glutamine, penicillin/streptomycin, 4×10$^{-4}$ M monothioglycerol (Sigma-Aldrich), and 50 μg/ml ascorbic acid (Sigma-Aldrich), to prepare embryoid bodies (EBs).
(Day 1 to Day 4)
The obtained EBs were collected and washed, followed by performing culture for additional 3 days in StemPro-34 supplemented with 5 ng/ml bFGF, 10 ng/ml BMP-4, 2 mM glutamine, penicillin/streptomycin, 4×10$^{-4}$ M monothioglycerol, and 50 μg/ml ascorbic acid, thereby inducing primitive streak/mesoderm formation.
(Day 4 to Day 8)
On Day 4, EBs were collected again, and then cultured again for 4 days in StemPro-34 supplemented with vascular endothelial growth factor (VEGF; 10 ng/ml), bFGF (1 ng/ml), interleukin-6 (IL-6; 10 ng/ml), IL-3 (40 ng/ml), IL-11 (5 ng/ml), stem cell factor (SCF; 100 ng/ml), and human FLT3 ligand (FLT3L; 100 ng/ml), for specialization and development into hematopoietic progenitor cells.
(Day 8 to Day 15)
On Day 8, EBs were transferred to an environment of 5% $CO_2$/air, and cultured for additional 7 days in StemPro-34 supplemented with VEGF (10 ng/ml), erythropoietin (EPO; 4 U/ml), thrombopoietin (TPO; 50 ng/ml), SCF (100 ng/ml), FLT3L (100 ng/ml), IL-6 (10 ng/ml), IL-11 (5 ng/ml), and IL-3 (40 ng/ml), for maturation (maturation into erythroblasts and megakaryocytic progenitor cells) and expansion into hematopoietic progenitor cells. The cells were then incubated at 37° C. for 5 to 10 minutes with 0.25% Trypsin-EDTA, and dissociated using a 1000-ml pipette to prepare a single-cell suspension. The dissociated cells were passed through a 70-μm filter, and the collected cells were then evaluated by flow cytometry.

Among the cells obtained, 12 cell lines showing high efficiency of differentiation into CD43-positive cells were designated "High productive lines", and 12 cell lines showing low efficiency of differentiation into CD43-positive cells were designated "Nonproductive lines". These cell lines were used in the following assay. The "High productive lines" and "Nonproductive lines" are shown below in Table 4. In each group, the cell lines are shown in the order of higher to lower efficiencies of differentiation into CD43-positive cells.

TABLE 4

| High productive lines and Nonproductive lines | |
|---|---|
| High productive lines (12 cell lines) | Nonproductive lines (12 cell lines) |
| 585A1 | 589B1 |
| H9 | 648B1 |
| TIG1204F1 | 751A3 |
| KRV-1 | 451F3 |
| khES3 | 427F1 |
| 7-KE2 | 609A1 |
| TIG1074F1 | 744A2 |
| 201B6 | 751B4 |
| 454E2 | 783F1 |
| 610B1 | 784D1 |
| 665A7 | 246G1 |
| 253G4 | 588A4 |

Example 4

Identification of Marker Gene Indicating High Efficiency of Differentiation into Hematopoietic Stem Cells and/or Hematopoietic Progenitor Cells From the 12 High productive lines showing high efficiency of differentiation into hematopoietic stem cells and/or hematopoietic progenitor cells and the 12 Nonproductive lines showing low efficiency of differentiation into hematopoietic stem cells and/or hematopoietic progenitor cells, RNA was collected, and the collected RNA was subjected to measurement/analysis of RNA expression using a microarray (Agilent technology). Significance tests by statistical analysis were carried out using Gene spring 12.1 (Agilent technologie), wherein significance for each gene or probe was assumed based on satisfaction of the following standards: p<0.05 (unpaired t-test), False discovery ratio (FDR: according to the Benjamini-Hochberg method)<0.05, and Fold change >2.

As a result, based on comparison between the High productive lines and the Nonproductive lines, IGF2 was identified as the gene showing the largest difference in the gene expression between these two groups and showing positive correlation with the High productive lines.

Example 5

Identification of Marker Genes Showing Correlation with IGF2

According to Example 4, it was found that the expression level of IGF2 is positively correlated with high efficiency of differentiation of iPS/ES cells into hematopoietic stem cells and/or hematopoietic progenitor cells. In order to identify other genes that are positively correlated with high efficiency of differentiation into hematopoietic stem cells and/or hematopoietic progenitor cells, the same microarray data were used to find genes whose expression changes in correlation with that of IGF2.

The analysis was carried out by SPSS statistics (IBM), wherein significance for each gene was assumed at p<0.05 (unpaired t-test). Correlation of expression between genes was evaluated using the Pearson correlation coefficient.

As a result, it was found that iPS/ES cell lines showing high expression of IGF2 also show high expression of T, HOXB4, GATA2, CEBPA, MESP1, CDX2, BMP4, EOMES, SOX17, GATA6, GATA4, SNAI2, and the like (FIG. 2).

Example 6

Confirmation of Capacity to Differentiate into Blood Cells

In order to confirm the capacity to differentiate into blood cells, a colony formation assay was carried out using hematopoietic progenitor cells prepared by differentiation induction of 4 ES cell lines and 35 iPS cell lines. The induction of differentiation from the ES cells and the iPS cells into the hematopoietic progenitor cells was carried out by the following process.

(Day 0 to Day 1)

The obtained iPS cells were subjected to culture of small clusters (10 to 20 cells) of iPS cells containing no feeder cells for 24 hours using a 6-well low-cluster plate (Corning Incorporated) under the conditions of 37° C., 5% $CO_2$, 5% $O_2$, and 90% $N_2$ in an aggregation medium composed of StemPro-34 (Invitrogen) supplemented with human bone morphogenetic protein-4 (BMP-4; 10 ng/ml), Y27632 (10 μM), 2 mM glutamine, penicillin/streptomycin, $4\times10^{-4}$ M monothioglycerol (Sigma-Aldrich), and 50 μg/ml ascorbic acid (Sigma-Aldrich), to prepare embryoid bodies (EBs).

(Day 1 to Day 4)

The obtained EBs were collected and washed, followed by performing culture for additional 3 days in StemPro-34 supplemented with 5 ng/ml bFGF, 10 ng/ml BMP-4, 2 mM glutamine, penicillin/streptomycin, $4\times10^{-4}$ M monothioglycerol, and 50 μg/ml ascorbic acid, thereby inducing primitive streak/mesoderm formation.

(Day 4 to Day 8)

On Day 4, EBs were collected again, and then cultured again for 4 days in StemPro-34 supplemented with vascular endothelial growth factor (VEGF; 10 ng/ml), bFGF (1 ng/ml), interleukin-6 (IL-6; 10 ng/ml), IL-3 (40 ng/ml), IL-11 (5 ng/ml), stem cell factor (SCF; 100 ng/ml), and human FLT3 ligand (FLT3L; 100 ng/ml), for specialization and development into hematopoietic progenitor cells.

(Day 8 to Day 15)

On Day 8, EBs were transferred to an environment of 5% $CO_2$/air, and cultured for additional 7 days in StemPro-34 supplemented with VEGF (10 ng/ml), erythropoietin (EPO; 4 U/ml), thrombopoietin (TPO; 50 ng/ml), SCF (100 ng/ml), FLT3L (100 ng/ml), IL-6 (10 ng/ml), IL-11 (5 ng/ml), and IL-3 (40 ng/ml), for maturation (maturation into erythroblasts and megakaryocytic progenitor cells) and expansion into hematopoietic progenitor cells. The cells were then incubated at 37° C. for 5 to 10 minutes with 0.25% Trypsin-EDTA, and dissociated using a 1000-ml pipette to prepare a single-cell suspension. The dissociated cells were passed through a 70-μm filter, and cells in the CD43$^+$ CD34$^+$ CD38$^-$ lineage marker$^-$ fraction (hematopoietic progenitor cells) were collected by flow cytometry Aria II (Beckton Dickinson).

Subsequently, in order to carry out a colony formation assay, the cells in the CD43$^+$ CD34$^+$ CD38$^-$ lineage marker$^-$ fraction were plated in 2 ml of methyl cellulose medium supplemented with stem cell factor (SCF), G-CSF, GM-CSF, interleukin-3 (IL-3), IL-6, and erythropoietin (MethoCult H4435) using a 35-mm culture dish. Fifteen days after the plating, the number of mixed colonies were counted under the microscope to evaluate the pluripotency of the iPS/ES cell-derived hematopoietic progenitor cells.

Eighteen cell lines showing large numbers of mixed colonies were designated "Good lines", which have high capacity to differentiate into blood cells, and 18 cell lines showing small numbers of mixed colonies were designated "Bad lines", which have low capacity to differentiate into blood cells. These cell lines were used in the following assay. The "Good lines" and the "Bad lines" are shown below in Table 5. In each group, the cell lines are shown in the order of larger to smaller numbers of mixed colonies.

TABLE 5

| Good lines and Bad lines | |
| --- | --- |
| Good lines (18 cell lines) | Bad lines (18 cell lines) |
| 751A3 | 427F1 |
| 783F1 | khES1 |
| 751B4 | TIG1204F1 |
| 692D2 | H9 |
| 783A2 | Kep1 |
| 744A2 | 454E2 |
| 744B9 | 253G1 |
| 609A2 | KRV-1 |
| 585B1 | 457C1 |
| 784D1 | 7-KE2 |
| 609A1 | 201B7 |
| 648B1 | TIG1074F1 |
| 665A7 | 246G1 |
| 451F3 | 409B2 |
| 610B1 | 201B6 |
| 606A1 | 253G4 |
| 648A1 | 404C2 |
| khES3 | 588A4 |

It was found that the number of mixed colonies is also correlated with the capacity to differentiate into platelets and the capacity to differentiate into erythrocytes (that is, the Good lines showed high capacity to differentiate into platelets and erythrocytes, and the Bad lines showed low capacity to differentiate into platelets and erythrocytes).

Example 7

Identification of Marker Genes Indicating High Capacity to Differentiate into Blood Cells From the 18 Good lines having high capacity to differentiate into blood cells and the 18 Bad lines having low capacity to differentiate into blood cells, RNA was collected, and the collected RNA was subjected to measurement/analysis of RNA expression using a microarray (Agilent technology). Significance tests by statistical analysis were carried out using Gene spring 12.1 (Agilent technologie), wherein significance for each gene or probe was assumed based on satisfaction of the following standards: p<0.05 (unpaired t-test), False discovery ratio (FDR: according to the Benjamini-Hochberg method)<0.05, and Fold change >2.

As a result, as genes showing significantly higher expression in Good lines than in Bad lines, CTSF, FAM19A5, TRIM58, TCERG1L, and the like were identified (FIG. 3).

Example 8

Identification of Methylation Associated with Capacity to Differentiate into Blood Cells The methylation states in the genomes of the 18 Good lines having high capacity to differentiate into blood cells and the 18 Bad lines having low capacity to differentiate into blood cells were investigated using an Infinium methylation beads array 450 k (Illumina). Significance tests by statistical analysis were carried out using Gene spring 12.1 (Agilent technologie), wherein significance for each gene or probe was assumed based on satisfaction of the following standards: p<0.05 (Mann Whitney u test), False discovery ratio (FDR: according to the Benjamini-Hochberg method)<0.05, and a difference in methylation between the groups (β value: mini 0 to max 1) of not less than 0.2.

As a result, it was found that the number of mixed colonies is significantly positively correlated with low methylation states of TRIM58, CSMD1, and FAM19A5.

Among the 35 iPS cell lines shown in Table 3, Good lines (good-HDF-iPS (4 cell lines)) and Bad lines (bad-HDF-iPS (12 cell lines)) derived from HDFs were selected, and the methylation states their genomes were investigated using an Infinium methylation beads array 450 k (Illumina). The good-HDF-iPS and bad-HDF-iPS are shown below in Table 6. In each group, the cell lines are shown in the order of larger to smaller numbers of mixed colonies.

TABLE 6 good-HDF-iPS and bad-HDF-iPS

| good-HDF-iPS (4 cell lines) | bad-HDF-iPS (12 cell lines) |
|---|---|
| 751A3 | 589B1 |
| 751B4 | 427F1 |
| 609A2 | TIG1204F1 |
| 609A1 | 253G1 |
| — | 201B7 |
| — | TIG1074F1 |
| — | 246G1 |
| — | 409B2 |
| — | 201B6 |
| — | 253G4 |
| — | 404C2 |
| — | 588A4 |

As a result, it was found that, also in the HDF-derived iPS cell lines, the number of mixed colonies is significantly positively correlated with low methylation states of TRIM58, CSMD1, and FAM19A5 (FIG. 4).

INDUSTRIAL APPLICABILITY

By the method of the present invention, differentiation of pluripotent stem cells into hematopoietic stem cells and/or hematopoietic progenitor cells can be more efficiently induced. In addition, iPS cells in an undifferentiated state before differentiation induction can be evaluated for their capacity to differentiate into blood (efficiency of differentiation into hematopoietic stem cells and/or hematopoietic progenitor cells, and capacity to differentiate into blood cells). By culturing induced pluripotent stem cells having high capacity to differentiate into selected hematopoietic stem cells, hematopoietic progenitor cells, or blood cells, and inducing their differentiation into the hematopoietic stem cells, hematopoietic progenitor cells, or blood cells, a large amount of blood-related cells can be efficiently supplied, and used in transplantation therapy and the like of various blood-related diseases.

The present invention was described with a focus on preferred modes, but the fact that the preferred modes can be modified is evident to those skilled in the art. The present invention is meant to be one which may also be carried out by methods other than those described in detail in the present description. Accordingly, the present invention includes all modifications included within the scope of the Abstracts and the attached Claims.

The content disclosed in an arbitrary publication (including patents and patent applications) cited in the present description is hereby incorporated, by reference, in its entirety to the same extent as in cases where the publication is disclosed in the present description.

What is claimed is:

1. A method for producing hematopoietic stem cells and/or hematopoietic progenitor cells from pluripotent stem (PS) cells, said method comprising:
   (a) measuring the expression level(s) of one or more genes selected from the group consisting of TRIM58, CTSF, FAM19A5, and TCERG1L genes in candidate PS cells;
   (b) selecting a PS cell(s) in which the expression level(s) of the gene(s) measured in Step (a) is/are equivalent to or higher than the expression level(s) in iPS cells or embryonic stem (ES) cells which are known to have high capacity to differentiate into blood cells, and/or selecting a PS cell(s) in which the expression level(s) of the gene(s) measured in Step (a) is/are higher than the expression level(s) in iPS cells or ES cells which are known to have low capacity to differentiate into blood cells; and
   (c) culturing the selected PS cells in the presence of insulin-like growth factor 2 (IGF2).

2. The method according to claim 1, wherein said step of culturing the selected PS cells in the presence of IGF2 comprises the steps of:
   (i) culturing the selected PS cells in a medium supplemented with BMP4 and IGF2;
   (ii) culturing cells obtained in Step (i) in a medium supplemented with BMP4, bFGF, and IGF2;
   (iii) culturing cells obtained in Step (ii) in a medium supplemented with VEGF, bFGF, IL-6, IL-3, IL-11, SCF, Flt3L, and IGF2; and
   (iv) culturing cells obtained in Step (iii) in a medium supplemented with VEGF, IL-6, IL-3, IL-11, SCF, Flt3L, EPO, TPO, and IGF2.

3. The method according to claim 1, wherein, in said step of culturing pluripotent stem cells, said pluripotent stem cells are cultured in a form of embryoid bodies.

4. The method according to claim 1, wherein said pluripotent stem cells are iPS cells.

5. The method according to claim 4, wherein said iPS cells are human iPS cells.

6. The method according to claim 1, wherein said sample of induced pluripotent stem cells are human iPS cells.

7. The method according to claim 1, wherein said blood cells are one or more kinds of cells selected from the group consisting of erythrocytes, platelets, monocytes, T cells, B cells, NK cells, neutrophils, eosinophils, basophils, granulocytes, and macrophages.

8. The method according to claim 1, wherein said iPS cells or ES cells which are known to have high capacity to differentiate into blood cells are one or more kinds of cells selected from the group consisting of 751A3, 783F1, 751B4, 692D2, 783A2, 744A2, 744B9, 609A2, 585B1, 784D1, 609A1, 648B1, 665A7, 451F3, 610B1, 606A1, 648A1, and khES3.

9. The method according to claim 1, wherein said iPS cells or ES cells which are known to have low capacity to differentiate into blood cells are one or more kinds of cells selected from the group consisting of 427F1, khES1, TIG1204F1, H9, Kep1, 454E2, 253G1, KRV-1, 457C1, 7-KE2, 201B7, TIG1074F1, 246G1, 409B2, 201B6, 253G4, 404C2, and 588A4.

10. A method for producing hematopoietic stem cells and/or hematopoietic progenitor cells from pluripotent stem (PS) cells, said method comprising
(a) measuring the DNA methylation state(s) of TRIM58, CSMD1, and/or FAM19A5 gene(s) in candidate PS cells;
(b) selecting a PS cell(s) in which the DNA methylation level(s) measured in Step (a) is/are equivalent to or lower than the DNA methylation level(s) in iPS cells or ES cells which are known to have high capacity to differentiate into blood cells, and/or selecting a PS cell(s) in which the DNA methylation level(s) measured in Step (a) is/are lower than the DNA methylation level(s) in iPS cells or ES cells which are known to have low capacity to differentiate into blood cells; and
(c) culturing the selected PS cells in the presence of insulin-like growth factor 2 (IGF2).

11. The method according to claim 10, wherein said step of culturing the selected PS cells in the presence of IGF2 comprises the steps of:
(i) culturing the selected PS cells in a medium supplemented with BMP4 and IGF2;
(ii) culturing cells obtained in Step (i) in a medium supplemented with BMP4, bFGF, and IGF2;
(iii) culturing cells obtained in Step (ii) in a medium supplemented with VEGF, bFGF, IL-6, IL-3, IL-11, SCF, Flt3L, and IGF2; and
(iv) culturing cells obtained in Step (iii) in a medium supplemented with VEGF, IL-6, IL-3, IL-11, SCF, Flt3L, EPO, TPO, and IGF2.

12. The method according to claim 10, wherein, in said step of culturing pluripotent stem cells, said pluripotent stem cells are cultured in a form of embryoid bodies.

13. The method according to claim 10, wherein said pluripotent stem cells are iPS cells.

14. The method according to claim 13, wherein said iPS cells are human iPS cells.

15. The method according to claim 10, wherein said blood cells are one or more kinds of cells selected from the group consisting of erythrocytes, platelets, monocytes, T cells, B cells, NK cells, neutrophils, eosinophils, basophils, granulocytes, and macrophages.

16. The method according to claim 10, wherein said iPS cells or ES cells which are known to have high capacity to differentiate into blood cells are one or more kinds of cells selected from the group consisting of 751A3, 783F1, 751B4, 692D2, 783A2, 744A2, 744B9, 609A2, 585B1, 784D1, 609A1, 648B1, 665A7, 451F3, 610B1, 606A1, 648A1, and khES3.

17. The method according to claim 10, wherein said iPS cells or ES cells which are known to have low capacity to differentiate into blood cells are one or more kinds of cells selected from the group consisting of 427F1, khES1, TIG1204F1, H9, Kep1, 454E2, 253G1, KRV-1, 457C1, 7-KE2, 201B7, TIG1074F1, 246G1, 409B2, 201B6, 253G4, 404C2, and 588A4.

\* \* \* \* \*

SEQUENCE LISTING

```
<160> NUMBER OF SEQ ID NOS: 5

<210> SEQ ID NO 1
<211> LENGTH: 5158
<212> TYPE: DNA
<213> ORGANISM: Homo sapiens

<400> SEQUENCE: 1
gggagacggt gcgggcggcc gggagcgcag ccctccggga ggcgggtcat ggcctgggcg     60
ccgcccgggg agcggctgcg cgaggatgcg cggtgcccgg tgtgcctgga tttcctgcag    120
```

| | |
|---|---|
| gagccggtca gcgtggactg cggccacagc ttctgcctca ggtgcatctc cgagttctgc | 180 |
| gagaagtcgg acggcgcgca gggcggcgtc tacgcctgtc cgcagtgccg ggcccccttc | 240 |
| cggccctcgg gctttcgccc caaccggcag ctggcgggcc tggtggagag cgtgcggcgg | 300 |
| ctggggttgg gcgcggggcc cggggcgcgg cgatgcgcgc ggcacggcga ggacctgagc | 360 |
| cgcttctgcg aggaggacga ggcggcgctg tgctgggtgt gcgacgccgg ccccgagcac | 420 |
| aggacgcacc gcacggcgcc gctgcaggag gccgccggca gctaccaggt aaagctccag | 480 |
| atggctctgg aacttatgag gaaagagttg gaggacgcct tgactcagga ggccaacgtg | 540 |
| gggaaaaaga ctgtcatttg gaaggagaaa gtggaaatgc agaggcagcg cttcagattg | 600 |
| gagtttgaga agcatcgtgg ctttctggcc caggaggagc aacggcagct gaggcggctg | 660 |
| gaggcggagg agcgagcgac gctgcagaga ctgcgggaga gcaagagccg gctggtccag | 720 |
| cagagcaagg ccctgaagga gctggcggat gagctgcagg agaggtgcca gcgcccggcc | 780 |
| ctgggtctgc tggagggtgt gagaggagtc ctgagcagaa gtaaggctgt cacaaggctg | 840 |
| gaagcagaga acatccccat ggaactgaag acagcatgct gcatccctgg gaggagggag | 900 |
| ctcttaagga agttccaagt ggatgtaaag ctggatcccg ccacggcgca cccgagtctg | 960 |
| ctcttgaccg ccgacctgcg cagtgtgcag gatggagaac catggaggga tgtccccaac | 1020 |
| aaccctgagc gatttgacac atggccctgc atcctgggtt tgcagagctt ctcatcaggg | 1080 |
| aggcattact gggaggttct ggtgggagaa ggagcagagt ggggtttagg ggtctgtcaa | 1140 |
| gacacactgc caagaaaggg ggaaaccacg ccatctcctg agaatggggt ctgggccctg | 1200 |
| tggctgctga agggaatga gtacatggtc cttgcctccc catcagtgcc tcttctccaa | 1260 |
| ctggaaagtc ctcgctgcat tgggattttc ttggactatg aagccggtga atttcattc | 1320 |
| tacaatgtca cagatggatc ttatatctac acattcaacc aactcttctc tggtcttctt | 1380 |
| cggccttact ttttcatctg tgatgcaact cctcttatct tgccaccac aacaatagca | 1440 |
| gggtcaggaa attgggcatc cagggatcat ttagatcctg cttctgatgt aagagatgat | 1500 |
| catctctaaa attctgttcc caagatgcag tcctagcgta gcgaacgttc ctggagtggg | 1560 |
| gtgaaggata tcaatatact aagttttaac agataccca tttaggtcag cacttgattc | 1620 |
| gttgttgctg tgaaatatgt ccatgggaca aagagggaa tatgaaatat ttgcatatgg | 1680 |
| gaagattata gagcataata attttgtaaa tggagcaatc tcaacctcta tttctagatc | 1740 |
| acattttctt gatgtcttcc ttcaaattaa tgaccttgga ttacataagg atttctatgc | 1800 |
| attcattata atttgttatt cctttcaata tccttgtatt tcaaatcttc catataagaa | 1860 |
| ttagacatgg caattcttaa attgattcag aatggtctga tactattcca gtatcacctc | 1920 |
| cttaattctg tttctcctcg ttttcctgat tttccttctc attctctcct tccccgctct | 1980 |
| gtctctctct ccctgtcact ctctctctct tgttccttat ttttgtttc ttacctctta | 2040 |
| ctgtttaacc tgttgcttcc ttctggatta atacatttag agccattcct ttatatggtc | 2100 |
| acatttccta tgactttact caattacttt taaaatcctt tctattctga gactaatttt | 2160 |
| taagaattac aaagctcatt cttctgaatc taatatcact aactcctaga cttttttccgt | 2220 |
| tttctttgga tacactttaa gtaggaattt atcagaattt tcattcaact cgttctttaa | 2280 |
| tgcagatatt tactagttat aagaccttaa ggctgggtgc agtggctcac gcctgtaatc | 2340 |
| ccagcacttt gggaggctga ggcgggtgga tcacaagctc aggagttcaa gaccagcctg | 2400 |
| gccaacatgg tgaaaccctg tctctactaa aaaaaaaaa aaaatagaaa aattagctgg | 2460 |

```
gcatggtggc aggagcctgt aatcccagct attctggagg tggagacagg agaattgctt    2520
gaaccctgga ggcggaggtt gcagtgagcc aatatctcac cactgtactc cagcccagtg    2580
cgagactcca tctcaaaaaa gaaaaaagac ctcaaacaac acttctctct ctcttttagc    2640
tgcttgttat ggttcctata catggaacaa ttatactggc ctcactgtgt tatggtaaat    2700
atttaaggtc atatttgata ttgctggttt gaattcagct tttccattta aatacattat    2760
aatgatgatg atgaaatcat gataatattt aacttatttt taaagtatat tctgtacctt    2820
tccaacaaaa aggttaaaag tcattgaagg ctaaccttac tgccttcttt gtatcactgt    2880
cttctaaata attattatgt ctgggtacag tggctcacgc ctgtaatccc agcactttgg    2940
gaggccgagg tgggcagatc acgaggtcag gagattgaga ccatcctggc taacacagtg    3000
aaaccccgtc tctactaaaa atacaaaaag aaattagctg ggcgtggtgg tgggtgcctg    3060
ttgtcccagc tacttgggag gctgaggcag gagaatggca tgaacccagg aggcagagct    3120
tgtagtgagc cgagatcgcg ccactgcact ccagccgggg caacagagca agactccatc    3180
tcaaaaataa ataaataaat aaataaataa ataaataaat aaataaatat tacacaaatg    3240
ctaaaatgtt taaatggtaa atgcttcaat gctaaccaaa tattaattaa tggcaaatta    3300
tttaacatta tctgataata atctgcagaa ggtttaattt tcctcctcaa tttgaagttc    3360
aagatgtttt tctcttccag ggagattttt tcgactgaca tctttaactt accttccaat    3420
catattacta acgtagcctt cttcctagat tttttaattg tttgatcatg agcgaacact    3480
tctactctct gtgatagatt tgcaaacaga ggaaataacg catcctcgtg tccctcttct    3540
tggtgttcca caggccatgt gtgccctagc cctcgttcat gcaaggtctg tgtagggaag    3600
gtggacttca gctcagcaac agcatcccct tcccacaggga tcaggtgggt ggcttgagat    3660
accccttcca tggggcacca cccattcagt gagacgggga agccctgggt gggagggaga    3720
acacctccac atgtcttcta ctctctccat aggatggaat gagtgtccca gtcccaggag    3780
tatccatttc ccactgtgta gcccagtact ctggtctcac tgtctctgct gaatcctgtc    3840
tcactgtgca tattattgtg gtttatatca gtcagtaaac caatgtgagt cttcatctct    3900
tgcattctta ggttcatagt tttgtgtgtc tcctgtaatg actcttctct ttcccttttcc    3960 aactcctgaa agattgccac tatttcctct ggaactttgt ttcgttacca gcaaaatcct    4020
cgacatccat acccgtttcc tggctttccc tctcctttcc tctgaatggt agtcttttat    4080
attcagctgt ccacttgaca tcaaaataga cattttgaac tcaatttgcc taaaacttac    4140
ccacaaattt ctccccaagt ctctccctaa ctgcaacaac aaaaaccaca ggcttctccc    4200
tgtcactgga tggcaactcc attcttttga ttgcttaagc caggcatccg attgagtact    4260
ttcttgattt ctccagccca catccagtcc atcggcaagc cctgttggtc ctaccttcag    4320
aatatgtccg gggttcagtt gtcctggcca ccctgctgct gtaaccatgg tcagaactcc    4380
atcctgcccc tctggattat gactttcgtt tcctcacagt ggtcctgctt gggctctagg    4440
cccttccact cccattctct ctacagcagc tgggctgatt cctttagcac caaggatat    4500 gttggcatca cagtgactta gataccatca caaagacctc ccattcaact tagagtgaaa    4560
gtcagaatcc tcacagtgaa tccccaggcc ctagaggatg tgaaccccca ggccctagag    4620
gatctgaacc cccatccctc ctctgattat ctctcccacc cccacttccc tttgcattct    4680
gctccagctg ccctggcctc atggctgggt ttccaccaaa gcaggcactt cccatcacag    4740
ggccatttcc ccgcctgtgg cttctgcttg acattccctt ttccctgata tccccttgac    4800
tcattattcc cttctcttcct taactcttct gagatccagc ttctcagtga taccacacag    4860
```

| | | | |
|---|---|---|---|
| ccctactccc | cccagagccc | atctagagct | cacctttcca gtcgcccttg ccaggctcag | 4920 |
| tggaggctct | ttgttcccca | tacagtacgt | gtcgtcgtac tatattgtta ggcttattta | 4980 |
| atttatgtat | gttttgcctt | tttgtgctaa | atgtaaacac cacaagggga ggtatctttg | 5040 |
| tctgttgaca | atgatacatt | caatgtttct | caagcacccc caatgctggt ttgtatgtgg | 5100 |
| ttatcattca | atctgtattt | gttgaatgaa | taaatgattg actatgtgga gagcaaaa | 5158 |

<210> SEQ ID NO 2
<211> LENGTH: 2032
<212> TYPE: DNA
<213> ORGANISM: Homo sapiens

<400> SEQUENCE: 2

| | | | |
|---|---|---|---|
| ggaggactca | ggccccgctg | gccgcgggct | cggtacccgg tgggtcggtg gagcgtctgt | 60 |
| tgggtccggg | ccgccggctt | cgccctcgcc | atggcgccct ggctgcagct cctgtcgctg | 120 |
| ctggggctgc | tcccgggcgc | agtggccgcc | ccgcccagc cccgagccgc cagctttcag | 180 |
| gcctgggggc | cgccgtcccc | ggagctgctg | gcgcccaccc gcttcgcgct ggagatgttc | 240 |
| aaccgcggcc | gggctgcggg | gacgcgggcc | gtgctgggcc ttgtgcgcgg ccgcgtccgc | 300 |
| cgggcgggtc | aggggtcgct | gtactccctg | gaggccaccc tggaggagcc accctgcaac | 360 |
| gaccccatgg | tgtgccggct | cccgtgtcc | aagaaaaccc tgctctgcag cttccaagtc | 420 |
| ctggatgagc | tcggaagaca | cgtgctgctg | cggaaggact gtggcccagt ggacaccaag | 480 |
| gttccaggtg | ctggggagcc | caagtcagcc | ttcactcagg gctcagccat gatttcttct | 540 |
| ctgtcccaaa | accatccaga | caacagaaac | gagactttca gctcagtcat ttccctgttg | 600 |
| aatgaggatc | ccctgtccca | ggacttgcct | gtgaagatgg cttcaatctt caagaacttt | 660 |
| gtcattacct | ataaccggac | atatgagtca | aaggaagaag cccggtggcg cctgtccgtc | 720 |
| tttgtcaata | acatggtgcg | agcacagaag | atccaggccc tggaccgtgg cacagctcag | 780 |
| tatggagtca | ccaagttcag | tgatctcaca | gaggaggagt tccgcactat ctacctgaat | 840 |
| actctcctga | ggaaagagcc | tggcaacaag | atgaagcaag ccaagtctgt gggtgacctc | 900 |
| gcccccacctg | aatgggactg | gaggagtaag | ggggctgtca caaaagtcaa agaccagggc | 960 |
| atgtgtggct | cctgctgggc | cttctcagtc | acaggcaatg tggagggcca gtggtttctc | 1020 |
| aaccagggga | ccctgctctc | cctctctgaa | caggagctct tggactgtga caagatggac | 1080 |
| aaggcctgca | tgggcggctt | gccctccaat | gcctactcgg ccataaagaa tttgggaggg | 1140 |
| ctggagacag | aggatgacta | cagctaccag | ggtcacatgc agtcctgcaa cttctcagca | 1200 |
| gagaaggcca | aggtctacat | caatgactcc | gtggagctga cccagaacga gcagaagctg | 1260 |
| gcagcctggc | tggccaagag | aggcccaatc | tccgtggcca tcaatgcctt tggcatgcag | 1320 |
| ttttaccgcc | acgggatctc | ccgccctctc | cggcccctct gcagcccttg gctcattgac | 1380 |
| catgcggtgt | tgcttgtggg | ctacggcaac | cgctctgacg ttcccttttg ggccatcaag | 1440 |
| aacagctggg | gcactgactg | gggtgagaag | ggttactact acttgcatcg tgggtccggg | 1500 |
| gcctgtggcg | tgaacaccat | ggccagctcg | gcggtggtgg actgaagagg ggcccccagc | 1560 |
| tcgggacctg | gtgctgatca | gagtggctgc | tgccccagcc tgacatgtgt ccaggcccct | 1620 |
| ccccggagg | tacagctggc | agagggaaag | gcactgggta cctcagggtg agcagagggc | 1680 |
| actgggctgg | ggcacagccc | ctgcttccct | gcacccatt cccaccctga agttctgcac | 1740 |
| ctgcaccttt | gttgaattgt | ggtagcttag | gaggatgtcg gggtgaaggg tggtatcttg | 1800 |

| | |
|---|---|
| gcagttgaag ctggggcaag aactctgggc ttgggtaatg agcaggaaga aaattttctg | 1860 |
| atcttaagcc cagctctgtt ctgcccccgc tttcctctgt ttgatactat aaattttctg | 1920 |
| gttcccttgg atttagggat agtgtccctc tccatgtcca ggaaacttgt aaccacccTT | 1980 |
| ttctaacagc aataaagagg tgtccttgtc ccgaaaaaaa aaaaaaaaaa aa | 2032 |

<210> SEQ ID NO 3
<211> LENGTH: 2620
<212> TYPE: DNA
<213> ORGANISM: Homo sapiens

<400> SEQUENCE: 3

| | |
|---|---|
| gggcccgggc gcggcggcgg cggcggcgga ggatggcgcg cgcggggccc gcacgtggag | 60 |
| gccggcgcgg gggcgcgggc agggccggct gctgagacgc gctgctgccc cccgcgcggg | 120 |
| cgccgcggct tcaatggcgc catcgcccag gaccggcagc cggcaagatg cgaccgccct | 180 |
| gcccagcatg tcctcaactt ctgggcgtt catgatcctg gccagcctgc tcatcgccta | 240 |
| ctgcagtcag ctggccgccg gcacctgtga gattgtgacc ttggaccggg acagcagcca | 300 |
| gcctcggagg acgatcgccc ggcagaccgc ccgctgtgcg tgtagaaagg ggcagatcgc | 360 |
| cggcaccacg agagcccggc ccgcctgtgt ggacgcaaga atcatcaaga ccaagcagtg | 420 |
| gtgtgacatg cttccgtgtc tggaggggga aggctgcgac ttgttaatca accggtcagg | 480 |
| ctggacgtgc acgcagcccg gcggaggat aaagaccacc acggtctcct gacaaacaca | 540 |
| gccccTGAGG ggccccggga gtggccttgg ctccctggag agcccacgtc tcagccacag | 600 |
| ttctccactc gcctcggact tcacccgttc tctgccgccc gcccactccg tttccctgtg | 660 |
| gtccgtgaag gacggcctca ggccttggca tcctgagctt cggtctgtcc agccgacccg | 720 |
| aggaggccgg actcagacac ataggcgggg ggcggcacct ggcatcagca atacgcagtc | 780 |
| tgtgggagcc cggccgcgcc cagcccccgc cgaccgtggc gttggccctg ctgtcctcag | 840 |
| aggaggagga ggaggaggca gctccggcag ccacagaagg ctgcagccca gcccgcctga | 900 |
| gacacgacgc ctgccccagg ggactgtcag gcacagaagc ggcctcctcc cgtgcccag | 960 |
| actgtccgaa ttgcttttat tttcttatac tttcagtata ctccatagac caaagagcaa | 1020 |
| aatctatctg aacctggacg caccctcact gtcagggtcc ctggggtcgc ttgtgcgggc | 1080 |
| gggagggcaa tggtggcaga gacatgctgg tggccccggc ggagcggaga gggcggccgt | 1140 |
| ggtggaggcc tccaccccag gagcaccccg cgcaccctcg gaggacgggc ttcggctgcg | 1200 |
| cggaggccgt ggcacacctg cgggaggcag cgacggcccc cacgcagacg ccgggaacgc | 1260 |
| aggccgcttt attcctctgt acttagatca acttgaccgt actaaaatcc ctttctgttt | 1320 |
| taaccagtta aacatgcctc ttctacagct ccattttTGA tagttggata atccagtatc | 1380 |
| tgccaagagc atgttgggtc tcccgtgact gctgcctcat cgatacccca tttagctcca | 1440 |
| gaaagcaaag aaaactcgag taacacttgt ttgaaagaga tcattaaatg tattttgcaa | 1500 |
| agcctaaagt tatatatttta acagtttta tatgttgtat atttgtagaa aatcctattt | 1560 |
| aacaattaac gtggcagtcc cggccgtcct gagagtcggg ccgagcccg tgtgtttctg | 1620 |
| aagactctgg gggtgggaca cggcggggag gtggtgcccc gcggacccg gggtgccagg | 1680 |
| cacggaaggc gggactctgg gagaagcgtg cggaggaccg tggcgtcggc gtcccggatg | 1740 |
| tgtcggtcgt gccggggag gccgggttcc cctcgctgcg ggccaggctt ggctcctgat | 1800 |
| tccctctctg gtccctgtat tggtcaacac ttgagcgtac aatatcttga acatgcttct | 1860 |
| tccaatgggt tttgtttccc atttcctgcc cctttcgcca ctcacggacc ttgaggccag | 1920 |

```
ttgacggccc ttctccccac gcctgtgtcc ccgcgttctg agaagtcctc tgtcttcgtg   1980
tcactaggtc cagaaagtcg cgccgggcag aggcgcaggc ggggccggca gggccgagga   2040
ataagcgaca attctggttt ttctcccctg gccgtcgttc gccagcctcc ttcatttcc    2100 tgagttcccg ctgaagtata tactacctat gagtccaatt aacatgagta ttatgctagt   2160
tctatcctac taaaaaaaac gtaaaaaaat aactatatag aagctgttcc agcaaccata   2220
gactgaagat acgaaagaaa atccatttat ttaagacctg ttccggtatc catgaggaca   2280
taatttacct ttcagtcacc acaaatttat aggcatttgt atcctggact aaaagaaggg   2340
gctgaggttg ggtttgtcat cacagagggg gtgggcctgg aaagggtcct tcccaagctg   2400
ccccggctcc ggcggccggg gccggcagcc tctgccagcc agcgtcctca cggcctcccc   2460
ctcgcctgtt tcttttgaaa gcaagtgtag acaccttcga gggcagagat cgggagattt   2520
aagatgttac agcatatttt tttttcttgt tttacagtat tcaattttgt gttgattcag   2580
ctaaattatg aaaaataaag aaaaactcct ttgataagca                         2620
```

<210> SEQ ID NO 4
<211> LENGTH: 2632
<212> TYPE: DNA
<213> ORGANISM: Homo sapiens

<400> SEQUENCE: 4

```
gagttcgctc cggagccgcg ccgccgccgg cccagcatct cgggcgcccg ccgccccgc     60 cgccgccgtc agcgcgggga tgtaggatgc aggcgggcgc caggttccag cggcggcggc   120
ggcagctgca gcagcagcag ccccggcggc ggcagcctct cctctggccg atggacgcag   180
agccgccgcc gccgccgccc tgggtctgga tggtgccggg ctcggccggg ctgctccggc   240
tcagcgcggg ggtcgtggtt ccccggtgc tgctcgcctc ggccccgccg cccgcggccc   300
cgctgctccc cggtctcccc ggctggccgg ccccgagcga gccggtgctc ccgctgctgc   360
cgctgccctc tgcgccagac tccgccgccg ccgccgccgc gcacccttc cccgcgctcc    420 acgggcagtg gctgtttggt ggccattctc cgtccctagg actgccccc tcttccacag    480 tggagctggt gccgtcttc ccacatctct gcccttctgc tcttgcaacc ctattggga    540 aaagttggat agacaaaagg attcctaact gtaagatctt ttttaataat tcctttgctc   600
tggactcaac gtggatacat cctgaggagt caaggttttt ccatgggcat gaaaagcctc   660
gtttgctggc aaatcaagta gctgtgtctc tgtccaggcc ggctcctgcc tccaggccgc   720
tccccacggt ggtgttagca cctcagccca tcccaggtgg ctgccataac agccttaagg   780
tgaccagcag ccccgccatt gccatcgcca ccgccgccgc cgctgccatg gtctccgtgg   840
accctgagaa cctccggggc ccgtccccct ccagcgtgca gccgcgccac ttcctgacct   900
tggcacccat caaaataccc ctccggacgt cccccgtctc agatacaagg acagagcggg   960
gccgagtggc ccgccctcct gccctgatgc tgcgggccca aagagccgg gatgagaca    1020 aagaagacaa ggagcctcca ccgatgctgg ggggaggaga ggacagcaca gccagaggca   1080
acaggccagt ggcctccacc ccggtgcccg gatccccctg gtgtgtggtc tggacgggcg   1140
atgaccgagt tttcttcttc aacccaacga tgcacctgtc tgtctgggag aagcccatgg   1200
acctgaagga ccgcggagac ctcaacagga tcattgagga cccgccccac aaacgcaagc   1260
tggaggcacc agcaactgac aacagcgatg ggtccagttc tgaagacaac agggaagacc   1320
aagatgtgaa aaccaagagg aaccggaccg aaggctgcgg gagtcccaag ccagaggagg   1380
```

| | |
|---|---|
| caaagagaga ggacaaaggc acaaggacgc cgcccccgca gatcctcctg cctctggagg | 1440 |
| agcgtgtgac ccacttccga gacatgctgc tggagagagg ggtatcagca ttttctacct | 1500 |
| gggagaaaga attacacaaa atcgtgtttg acccacgcta tctcctgctc aactctgagg | 1560 |
| aacgaaagca gatatttgaa cagtttgtca agacaagaat aaaagaagaa tacaaggaaa | 1620 |
| agaaaagtaa attgctgcta gccaaagaag aattcaagaa acttctagag gaatctaaag | 1680 |
| tgtctcccag gaccacgttt aaggagtttg cagagaaata cggccgggat cagaggttcc | 1740 |
| gacttgttca aaaagaaag gaccaggagc atttttcaa ccaattcata cttattctta | 1800 |
| agaaacggga caaggaaaac agactaaggc tgcggaaaat gagatgagtt tgtgaaaaaa | 1860 |
| tgcaataagc ccgggggttg accctgggcg tgccggggc gaggggtca cggtggagac | 1920 |
| ggacacgggc gtgggcggc cgagacctgc acggcccagc gggcaccggc actgcgggt | 1980 |
| cttcgttctc agaggattac tgtttcatat tgaagctctc tcttttgtac attcagagtt | 2040 |
| tgatgcattt ctaatcaccg tgatacgtcg atcccttaat tgttttaatt atgcaaatta | 2100 |
| cttgtaatat acacaaatta tcaatccact gcaggactgt ggggaagcag gaacgggagc | 2160 |
| ctctgtaaca atctcaaggc atttgtgtca tcacctaaga cgattggcga aaacttttct | 2220 |
| gaaaaccttt gtgaattact tcgtttctcc aggattcccg cagtgttgag gaattcctta | 2280 |
| ctctgtccct aggtctcagt ctcgtttctg agtagcagca ataggggtttt catcattcat | 2340 |
| catagtgaca actgtgagca ttccacacct ggaccgtgga tcacttacag gtttccaagg | 2400 |
| gtggccgcgc gttcctccca gaggggcgtc ccggcctgga gcaggagcc gtgttggttg | 2460 |
| ccaccggtcc tacttcaaaa gaattatttt gtacaaaatc atcatattaa tatttgagtt | 2520 |
| attttttattg tatgcccgga gtttgcatga gatttttct catcacccttt gtataaaaaa | 2580 |
| tttttaattt tttttaatca ataaatattt taaaccaaaa aaaaaaaaaa aa | 2632 |

<210> SEQ ID NO 5
<211> LENGTH: 14340
<212> TYPE: DNA
<213> ORGANISM: Homo sapiens

<400> SEQUENCE: 5

| | |
|---|---|
| cccactcgct ggctctctct ccagctgcct cctctccagg tctctcctgg ctgcgcgcgc | 60 |
| tcctctcccc gcttcccccc ctcccgcagc ctcgccgcct tggtgccttc ctgcccggct | 120 |
| cggccggcgc tcgtccccgg ccccggcccc gccagcccgg gtctccgcgc tcggagcagc | 180 |
| tcagccctgc agtggctcgg gacccgatgc tatgagaggg aagcgagccg gcgcccaga | 240 |
| ccttcaggag gcgtcggatg cgcggcgggt cttgggaccg ggctctctct ccggctcgcc | 300 |
| ttgccctcgg gtgattattt ggctccgctc atagccctgc cttcctcgga ggagccatcg | 360 |
| gtgtcgcgtg cgtgtggagt atctgcagac atgactgcgt ggaggagatt ccagtcgctg | 420 |
| ctcctgcttc tcgggctgct ggtgctgtgc gcgaggctcc tcactgcagc gaagggtcag | 480 |
| aactgtggag gcttagtcca gggtcccaat ggcactattg agagcccagg gtttcctcac | 540 |
| gggtatccga actatgccaa ctgcacctgg atcatcatca cggcgagcg caataggata | 600 |
| cagttgtcct tccatacctt tgctcttgaa gaagattttg atattttatc agtttacgat | 660 |
| ggacagcctc aacaagggaa tttaaaagtg agattatcgg gatttcagct gcctcctct | 720 |
| atagtgagta caggatctat cctcactctg tggttcacga cagacttcgc tgtgagtgcc | 780 |
| caaggtttca agcattatata tgaagtttta cctagccaca cttgtggaaa tcctggagaa | 840 |
| atcctgaaag gagttctgca tggaacgaga ttcaacatag gagacaaaat ccggtacagc | 900 |

```
tgcctccctg gctacatctt ggaaggccac gccatcctga cctgcatcgt cagcccagga    960
aatggtgcat cgtgggactt cccagctccc ttttgcagag ctgagggagc ctgcggagga   1020
accttacgcg ggaccagcag ctccatctcc agcccgcact tcccttcaga gtacgagaac   1080
aacgcggact gcacctggac cattctggct gagcccgggg acaccattgc gctggtcttc   1140
actgactttc agctagaaga aggatatgat ttcttagaga tcagtggcac ggaagctcca   1200
tccatatggc taactggcat gaacctcccc tctccagtta tcagtagcaa gaattggcta   1260
cgactccatt tcacctctga cagcaaccac cgacgcaaag gatttaacgc tcagttccaa   1320
gtgaaaaagg cgattgagtt gaagtcaaga ggagtcaaga tgctgcccag caaggatgga   1380
agccataaaa actctgtctt gagccaagga ggtgttgcat tggtctctga catgtgtcca   1440
gatcctggga ttccagaaaa tggtagaaga gcaggttccg acttcagggt tggtgcaaat   1500
gtacagtttt catgtgagga caattacgtg ctccagggat ctaaaagcat cacctgtcag   1560
agagttacag agacgctcgc tgcttggagt gaccacaggc ccatctgccg agcgagaaca   1620
tgtggatcca atctgcgtgg gcccagcggc gtcattacct cccctaatta tccggttcag   1680
tatgaagata atgcacactg tgtgtgggtc atcaccacca ccgacccgga caaggtcatc   1740
aagcttgcct ttgaagagtt tgagctggag cgaggctatg acaccctgac ggttggtgat   1800
gctgggaagg tgggagacac cagatcggtc ttgtacgtgc tcacgggatc cagtgttcct   1860
gacctcattg tgagcatgag caaccagatg tggctacatc tgcagtcgga tgatagcatt   1920
ggctcacctg gtttaaagc tgtttaccaa gaaattgaaa agggagggtg tggggatcct   1980
ggaatccccg cctatgggaa gcggacgggc agcagtttcc tccatggaga tacactcacc   2040
tttgaatgcc cggcggcctt tgagctggtg ggggagagag ttatcacctg tcagcagaac   2100
aatcagtggt ctggcaacaa gcccagctgt gtattttcat gtttcttcaa ctttacggca   2160
tcatctggga ttattctgtc accaaattat ccagaggaat atgggaacaa catgaactgt   2220
gtctggttga ttatctcgga gccaggaagt cgaattcacc taatctttaa tgattttgat   2280
gttgagcctc agtttgactt tctcgcggtc aaggatgatg gcattctga cataactgtc   2340
ctgggtactt tttctggcaa tgaagtgcct tcccagctgg ccagcagtgg gcatatagtt   2400
cgcttggaat tcagtctga ccattccact actggcagag ggttcaacat cacttacacc   2460
acatttggtc agaatgagtg ccatgatcct ggcattccta taaacggacg acgttttggt   2520
gacaggtttc tactcgggag ctcggttct ttccactgtg atgatggctt tgtcaagacc   2580
cagggatccg agtccattac ctgcatactg caagacggga cgtggtctg gagctccacc   2640
gtgccccgct gtgaagctcc atgtggtgga catctgacag cgtccagcgg agtcattttg   2700
cctcctggat ggccaggata ttataaggat tctttacatt gtgaatggat aattgaagca   2760
aaaccaggcc actctatcaa ataaactttt gacagatttc agacagaggt caattatgac   2820
accttggagg tcagagatgg gccagccagt tcgtccccac tgatcggcga gtaccacggc   2880
acccaggcac cccagttcct catcagcacc gggaacttca tgtacctgct gttcaccact   2940
gacaacagcc gctccagcat cggcttcctc atccactatg agagtgtgac gcttgagtcg   3000
gattcctgcc tggacccggg catccctgtg aacggccatc gccacggtgg agactttggc   3060
atcaggtcca cagtgacttt cagctgtgac ccggggtaca cactaagtga cgacgagccc   3120
ctcgtctgtg agaggaacca ccagtggaac cacgccttgc ccagctgcga cgctctatgt   3180
ggaggctaca tccaagggaa gagtggaaca gtcctttctc ctgggtttcc agatttttat   3240
```

```
ccaaactctc taaactgcac gtggaccatt gaagtgtctc atgggaaagg agttcaaatg    3300
atctttcaca cctttcatct tgagagttcc cacgactatt tactgatcac agaggatgga    3360
agtttttccg agcccgttgc caggctcacc gggtcggtgt tgcctcatac gatcaaggca    3420
ggcctgtttg gaaacttcac tgcccagctt cggtttatat cagacttctc aatttcgtac    3480
gagggcttca atatcacatt ttcagaatat gacctggagc catgtgatga tcctggagtc    3540
cctgccttca gccgaagaat tggttttcac tttggtgtgg gagactctct gacgttttcc    3600
tgcttcctgg gatatcgttt agaaggtgcc accaagctta cctgcctggg tggggccgc     3660
cgtgtgtgga gtgcacctct gccaaggtgt gtggccgaat gtggagcaag tgtcaaagga    3720
aatgaaggaa cattactgtc tccaaatttt ccatccaatt atgataataa ccatgagtgt    3780
atctataaaa tagaaacaga agccggcaag ggcatccacc ttagaacacg aagcttccag    3840
ctgtttgaag gagatactct aaaggtatat gatggaaaag acagttcctc acgtccactg    3900
ggcacgttca ctaaaaatga acttctgggg ctgatcctaa acagcacatc caatcacctg    3960
tggctagagt tcaacaccaa tggatctgac accgaccaag ttttcaact cacctatacc     4020
agttttgatc tggtaaaatg tgaggatccg ggcatcccta actacggcta taggatccgt    4080
gatgaaggcc actttaccga cactgtagtt ctgtacagtt gcaacccggg gtacgccatg    4140
catggcagca cacccctgac ctgtttgagt ggagacagga gagtgtggga caaaccacta    4200
ccttcgtgca tagcggaatg tggtggtcag atccatgcag ccacatcagg acgaatattg    4260
tcccctggct atccagctcc gtatgacaac aacctccact gcacctggat tatagaggca    4320
gacccaggaa agaccattag cctccatttc attgttttcg acacggagat ggctcacgac    4380
atcctcaagg tctgggacgg gccggtggac agtgacatcc tgctgaagga gtggagtggc    4440
tccgcccttc cggaggacat ccacagcacc ttcaactcac tcaccctgca gttcgacagc    4500
gacttcttca tcagcaagtc tggcttctcc atccagttct ccacctcaat tgcagccacc    4560
tgtaacgatc caggtatgcc ccaaaatggc acccgctatg agacagcag agaggctgga     4620
gacaccgtca cattccagtg tgaccctggc tatcagctcc aaggacaagc caaaatcacc    4680
tgtgtgcagc tgaataaccg gttctctttgg caaccagacc ctcctacatg catagctgct   4740
tgtggaggga atctgacggg cccagcaggt gttatttgt caccccaacta cccacagccg    4800
tatcctcctg ggaaggaatg tgactggaga gtaaaagtga acccggactt tgtcatcgcc    4860
ttgatattca aaagtttcaa catggagccc agctatgact tcctacacat ctatgaaggg    4920
gaagattcca acagccccct cattgggagt taccagggcc tcaggcccc agaaagaata     4980
gagagtagcg gaaacagcct gtttctggca tttcggagtg atgcctccgt gggcctttca    5040
gggttcgcca ttgaatttaa agagaaacca cgggaagctt gttttgaccc aggaaatata    5100
atgaatggga caagagttgg aacagacttc aagcttggct ccaccatcac ctaccagtgt   5160
gactctggct ataagattct tgaccccctca tccatcacct gtgtgattgg ggctgatggg    5220
aaaccctcct gggaccaagt gctgcccctcc tgcaatgctc cctgtggagg ccagtacacg    5280
ggatcagaag gggtagtttt atcaccaaac taccccccata attacacagc tggtcaaata   5340
tgcctctatt ccatcacggt accaaaggaa ttcgtggtct ttggacagtt tgcctatttc    5400
cagacagccc tgaatgattt ggcagaatta tttgatggaa cccatgcaca ggccagactt    5460
ctcagctcac tctcggggtc tcactcaggg gaaacattgc ccttggctac gtcaaatcaa    5520
attctgctcc gattcagtgc aaagagcggt gcctctgccc gcggcttcca cttcgtgtat    5580
caagctgttc ctcgtaccag tgacacccaa tgcagctctg tccccgagcc cagatacgga    5640
```

```
aggagaattg gttctgagtt ttctgccggc tccatcgtcc gattcgagtg caacccggga    5700
tacctgcttc agggttccac ggcgctccac tgccagtccg tgcccaacgc cttggcacag    5760
tggaacgaca cgatccccag ctgtgtggta ccctgcagtg gcaatttcac tcaacgaaga    5820
ggtacaatcc tgtcccccgg ctaccctgag ccatacggaa acaacttgaa ctgtatatgg    5880
aagatcatag ttacggaggg ctcgggaatt cagatccaag tgatcagttt tgccacggag    5940
cagaactggg actcccttga gatccacgat ggtggggatg tgaccgcacc cagactggga    6000
agcttctcag gcaccacagt accggcactg ctgaacagta cttccaacca actctacctg    6060
catttccagt ctgacattag tgtggcagct gctggtttcc acctggaata caaaactgta    6120
ggtcttgctg catgccaaga accagccctc cccagcaaca gcatcaaaat cggagatcgg    6180
tacatggtga cgacgtgct ctccttccag tgcgagcccg ggtacaccct gcagggccgt    6240
tcccacattt cctgtatgcc agggaccgtt cgccgttgga actatccgtc tccctgtgc    6300
attgcaacct gtggagggac gctgagcacc ttgggtggtg tgatcctgag ccccggcttc    6360
ccaggttctt accccaacaa cttagactgc acctggagga tctcattacc catcggctat    6420
ggtgcacata ttcagtttct gaattttct accgaagcta atcatgactt ccttgaaatt    6480
caaaatggac cttaccacac cagccccatg attggacaat ttagcggcac ggatctcccc    6540
gcggccctgc tgagcacaac gcatgaaacc ctcatccact tttatagtga ccattcgcaa    6600
aaccggcaag gatttaaact tgcttaccaa gcctatgaat tacagaactg tccagatcca    6660
cccccatttc agaatgggta catgatcaac tcggattaca gcgtggggca atcagtatct    6720
ttcgagtgtt atcctgggta cattctaata ggccatcctg tcctcacttg tcagcatggg    6780
atcaacagaa actggaacta ccctttttcca agatgtgatg ccccttgtgg gtacaacgta    6840
acttctcaga acggcaccat ctactcccct ggctttcctg atgagtatcc gatcctgaag    6900
gactgcattt ggctcatcac ggtgcctcca gggcacggag tttacatcaa cttcaccctg    6960
ttacagacgg aagctgtcaa cgattacatt gctgtttggg acggtcccga tcagaactca    7020
ccccagctgg gagttttcag tggcaacaca gccctcgaaa cggcgtatag ctccaccaac    7080
caagtcctgc tcaagttcca cagcgacttt tcaaatggag gcttctttgt cctcaatttc    7140
cacgcatttc agctcaagaa atgtcaacct ccccagcgg ttccacaggc agaaatgctt    7200
actgaggatg atgatttcga aataggagat tttgtgaagt accagtgcca ccccgggtac    7260
accttggtgg ggaccgacat tctgacttgc aagctcagtt cccagttgca gtttgagggt    7320
tctctcccaa catgtgaagc acaatgccca gcaaatgaag tccggactgg atcatcggga    7380
gtcattctca gtccagggta tccgggtaat tattttaact cccagacttg ctcttggagt    7440
attaaagtgg aaccaaacta caacattacc atctttgtgg acacatttca aagtgaaaag    7500
cagtttgatg cactggaagt gtttgatggt tcttctgggc aaagtcctct gctagtagtc    7560
ttaagtggga atcatactga acaatcaaat tttacaagca ggagtaatca gttatatctc    7620
cgctggtcca ctgaccatgc caccagtaag aaaggattca agattcgcta tgcagcacct    7680
tactgcagtt tgacccaccc cctgaagaat ggggtattc taaacaggac tgcaggagcg    7740
gttggaagca aagtgcatta ttttgcaag cctggatacc gaatggtcgg ccacagcaat    7800
gcaacctgta gacgaaaccc acttggcatg taccagtggg actccctcac gccactctgc    7860
caggctgtgt cctgtggaat cccagaatcc ccaggaaacg ttcatttac cgggaacgag    7920
ttcactttgg acagtaaagt ggtctatgaa tgtcatgagg gcttcaagct tgaatccagc    7980
```

-continued

```
cagcaagcaa cagccgtgtg tcaagaagat gggttgtgga gtaacaaggg gaagccgccc      8040
acgtgtaagc cggtcgcttg ccccagcatt gaagctcagc tctcagaaca tgtcatctgg      8100
aggctggttt caggatcctt gaatgagtac ggtgctcaag tattgctgag ctgcagtcct      8160
ggttactact tagaaggctg gaggctcctg cggtgccagg ccaatgggac gtggaacata      8220
ggagatgaga ggccaagctg tcgagttatc tcgtgtggaa gcctttcctt tcccccaaat      8280
ggcaacaaga ttggaacgtt gacagtttat ggggccacag ctatatttac gtgcaacacc      8340
ggctacacgc ttgtggggtc tcatgtcaga gagtgcttgg caaatgggct ctggagcggc      8400
agcgaaactc gatgtctggc tggccactgc ggttccccag acccgattgt gaacggtcac      8460
attagtggag atggcttcag ttacagagac acggtggttt accagtgcaa tcctggtttc      8520
cggcttgtgg gaacttccgt gaggatatgc ctgcaagacc acaagtggtc tggacaaacg      8580
cctgtctgtg tccccatcac atgtggtcac cctggaaacc ctgcccacgg attcactaat      8640
ggcagtgagt tcaacctgaa tgatgtcgtg aatttcacct gcaacacggg ctatttgctg      8700
cagggcgtgt ctcgagccca gtgtcggagc aacggccagt ggagtagccc tctgcccacg      8760
tgtcgagtgg tgaactgttc tgatccaggc tttgtggaaa atgccattcg tcacgggcaa      8820
cagaacttcc ctgagagttt tgagtatgga atgagtatcc tgtaccattg caagaaggga      8880
ttttacttgc tgggatcttc agccttgacc tgtatggcaa atggcttatg ggaccgatcc      8940
ctgcccaagt gtttggctat atcgtgtgga cacccagggg tccctgccaa cgccgtcctc      9000
actggagagc tgtttaccta tggcgccgtc gtgcactact cctgcagagg gagcgagagc      9060
ctcataggca acgacacgag agtgtgccag gaagacagtc actggagcgg ggcactgccc      9120
cactgcacag gaaataatcc tggattctgt ggtgatccgg ggaccccagc acatgggtct      9180
cggcttggtg atgactttaa gacaaagagt cttctccgct tctcctgtga atgggggcac      9240
cagctgaggg gctcccctga acgcacgtgt ttgctcaatg ggtcatggtc aggactgcag      9300
ccggtgtgtg aggccgtgtc ctgtggcaac cctggcacac ccaccaacgg aatgattgtc      9360
agtagtgatg gcattctgtt ctccagctcg gtcatctatg cctgctggga aggctacaag      9420
acctcagggc tcatgacacg gcattgcaca gccaatggga cctggacagg cactgctccc      9480
gactgcacaa ttataagttg tgggggatcca ggcacactag caaatggcat ccagtttggg      9540
accgacttca ccttcaacaa gactgtgagc tatcagtgta acccaggcta tgtcatggaa      9600
gcagtcacat ccgccactat tcgctgtacc aaagacggca ggtggaatcc gagcaaacct      9660
gtctgcaaag ccgtgctgtg tcctcagccg ccgccggtgc agaatggaac agtggaggga      9720
agtgatttcc gctggggctc cagcataagt tacagctgca tggacggtta ccagctctct      9780
cactccgcca tcctctcctg tgaaggtcgc ggggtgtgga aggagagat cccccagtgt      9840 ctccctgtgt tctgcggaga ccctggcatc cccgcagaag ggcgacttag tgggaaaagt      9900
ttcacctata gtccgaagt cttcttccag tgcaaatctc catttatact cgtgggatcc      9960
tccagaagag tctgccaagc tgacggcacg tggagcggca tacaacccac ctgcattgat     10020
cctgctcata cacctgccc agaccctggt acgccacact ttggaataca gaatagctcc     10080
agaggctatg aggttggaag cacgttttt tcaggtgcaa gaaaggcta ccatattcaa      10140 ggttccacga ctcgcacctg ccttgccaat ttaacatgga gtgggataca gaccgaatgt     10200
atacctcatg cctgcagaca gccagaaacc ccggcacacg cggatgtgag agccatcgat     10260
cttcctactt tcggctacac cttagtgtac acctgccatc caggcttttt cctcgcaggg     10320
ggatctgagc acagaacatg taaagcagac atgaaatgga caggaaagtc gcctgtgtgt     10380
```

```
aaaagtaaag gagtgagaga agttaatgaa acagttacta aaactccagt tccttcagat    10440 gtcttttttcg tcaattcact gtggaagggg tattatgaat atttagggaa aagacaaccc    10500
gccactctaa ctgttgactg gttcaatgca acaagcagta aggtgaatgc caccttcagc    10560
gaagcctcgc cagtggagct gaagttgaca ggcatttaca agaaggagga ggcccactta    10620
ctcctgaaag cttttcaaat taaaggccag gcagatattt ttgtaagcaa gttcgaaaat    10680
gacaactggg gactagatgg ttatgtgtca tctggacttg aaagaggagg atttactttt    10740
caaggtgaca ttcatggaaa agactttgga aaatttaagc tagaaaggca agatcccttta   10800 aacccagatc aagactcttc cagtcattac cacggcacca gcagtggctc tgtggcggct    10860
gccattctgg ttccttttctt tgctctaatt ttatcagggt ttgcattta cctctacaaa    10920 cacagaacga gaccaaaagt tcaatacaat ggctatgctg ggcatgaaaa cagcaatgga    10980
caagcatcgt ttgaaaaccc catgtatgat acaaacttaa aacccacaga agccaaggct    11040
gtgaggtttg acacaactct gaacacagtc tgtacagtgg tatagccctc agtgccccaa    11100
caggactgat tcatagccat acctctgatg gacaagcagt gattcctttg gtgccatata    11160
ccactctccc ttccactctg gctttactgc agcgatcttc aaccttgtct actggcataa    11220
gtgcagcggg gatctctact caaatgtgtc agggtcttct acggatcaaa ctacacatgc    11280
gttttcattc caaagtgggg ttctaaatgc ctggctgcat ctgtatgaaa tcaaggcaca    11340
ctccaggaag actgccacgt cgcgccaaca cgtcatactc aatgcctcag actttcatat    11400
ttctgtgttg ctgagatgcc tttcaatgca atcgtctggg ctcgtggata tgtccctcag    11460
gtgcggtgac agaatggtgg caccacgata tgtgttctct tgtgttgttt ttccttttta    11520 aaccccccatg aacacgaata ctctgaaaaa aataaaaagc tttctggaag aagacacctt    11580
tctgatagag gctcacacct acaaatgctt cactctgtcc ttccgagacc tgacaagctt    11640
tgaggacctc acagctcccc tgtgtgttca tctctaggga tgtttgcaat ttcccagtca    11700
gctgttctgt cgcagaatgt ttaatgcaca atttttttgca ctagtgtgtt atgaatgact    11760
aagattctga taaaaaaaat aaattattta cacagggttt atacacacta tccattgtat    11820
ataagcatta tttcatatta tcaagctaaa cattccccca tcagcttagt tggagtgtta    11880
gggaaaagta ttcctagata tggcacagat tttaaaagga aatacagtat tgaagagatt    11940 tatttttatta ttgcttcaat tagctccatt tacgtgttga attcattgaa gaggtccaat    12000
gagaaaaaaa cagaagcctc cttatttcac acgttttcct cctttagtac catcctcatc    12060
caattactgt ctctctgata ctacttaata gcagggggtt tgcagaaatt tctgtttgcc    12120
atgtaaaact gtgaatagta atttattttta gatagtcgat gaacttgtgg gttttagctc    12180
acaatgcagc cttcccttttt gcagtgtttt tttttgttt tttttttttt ttgtcttttta    12240 ctgtgccatc gatctttgat attgcattga agacaatat accacagtag caccttgaac    12300
tcagtgaaaa ttgttcagga tcaaaatacc aagtgttctt ttagagggaa ggaaaaagta    12360
cacacactct cctctcacaa tgatatattt tatacattca tttgttattt gtttcatgct    12420
ttatgattcc agatggaaag gtaatttcag tgacttttca agtttaaatt ccattatagg    12480
taaatgataa gttatgatgc aaataaaatc tataagatcc ccagggcaaa taaaaatcaa    12540
aacatgaagt agaagatgtg gccgtgaggt agtttatgta acaaattcaa agtgaaaatc    12600
atgtttactt ttacttatac ttatttgata aaaatatttt tgaaacgata gtacttattt    12660
tattatttga tatttcagtt cctattcaat tgtggcagat tttctctgtt tcacatttta    12720
```

```
gattggcgtt ggtaatagaa atgtcagaat gttcaaattg gccttcacgt tgtcggagtg    12780
aacacattga cacctagctt taagactgat ttatctgttg gtgtactgaa ggtttccatg    12840
taggacttca aatgtggaaa aggaaaagca gtcaggaaaa tggggcattc tttggagagt    12900
cacgcgtttt gattcggaca tttccgtaga gctcggctcc cagtgttgtg ttcctcggtc    12960
gaaagggtct ctgctgtttg gggactcact ggcctctcct agggactcct ttgtcttgtg    13020
aaccccacgc tgttggattc tgtatcatta tgctgaattc tctgcacagt tttccctggc    13080
caacctgccc acatccttgg agatttgctt tgccagtggg aatccttaca ttgctgtttc    13140
acagtagacg ggacgaggtc agcgggagtc gtgctcctaa cacacacatt gaacgaaaca    13200
gaagatgatt gaaagtgtga ggaggctcgt gtgcaaggga aacagggtt actatacata     13260 ttagtgtata tatatacata catatatata tatatatt gtacatatct aagtttgagt      13320
cattcaaact aggtgcaaaa tgctgacttc agagtctgaa ttaacatctc tgttcccata    13380
tccctgacct gctccctggt caacgatgct atgaaatcct gaaatgacag gacatacata    13440
catacaagaa accacatatc aaattagata tgattttcct ttgtgtgcaa agtcaaactg    13500
tcctagggtt gccagtttga agcatgttat ttaaatgaaa aaaaaaatca gtgaaattct    13560
cgtgtgagaa ttctgcctag tttcttccta aggttgtgtg cagtgttgaa cggcgtctcc    13620
gcaaggtgtt ggaggatctc attttagggc agtcaggagc tgtgcttgct gagttaggtc    13680
tagaagactc ttccctgaag gcaacgggaa cacgcgtgag ggacgcgacc acacactaac    13740
agaggacacg tgcttcagag ctgtttaaaa ctgctgcttg ttttacacac acatcttgcc    13800
tttttccagg ctagctgcaa taatttttt cttctgtaaa atatttgta aacaacaaca      13860 aaaagctatt ataaaaaggg ggtaaaaaaa agaacgctgg cattatgatc aggaaaaccc    13920
attgtcatcg ccgaccctcc ctcccgtccc accacacgct gctgtcacga cgtaggtgcg    13980
aaagaccttt ttgtacagag atatattttt tatgaagaat ttgtaaaatt attaaatatg    14040
ctgtaatttt ttgattaatg taggtacatt gttaaaaaat aaatgttttt acaatacaga    14100
actgtaattt tcccaataat gtaaaatgta ccatctctag ctgattttca gttccaatcc    14160
tattacacat gtattaatat taaagtggcc tgttaaaatg aacagtatct ttttttttgtc   14220 aaaaaaatta taaagagggt gtaatatagc ctgtgcaatg ccaccaatct ttaaagcaaa    14280
tcagagttct aattaaatat ttaattttag atttctaaaa aaaaaaaaaa aaaaaaaaaa    14340
```